US007081561B2

(12) United States Patent
Weisgraber et al.

(10) Patent No.: US 7,081,561 B2
(45) Date of Patent: Jul. 25, 2006

(54) GENE-TARGETED ANIMAL MODEL OF APOLIPOPROTEIN E4 DOMAIN INTERACTION AND USES THEREOF

(75) Inventors: Karl H. Weisgraber, Walnut Creek, CA (US); Robert V. Farese, San Francisco, CA (US); Robert Raffai, San Francisco, CA (US); Li-Ming Dong, Palo Alto, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/017,718

(22) Filed: Dec. 14, 2001

(65) Prior Publication Data

US 2002/0194628 A1 Dec. 19, 2002

Related U.S. Application Data

(60) Provisional application No. 60/276,861, filed on Mar. 16, 2001.

(51) Int. Cl.
*A01K 67/027* (2006.01)
*A01K 67/00* (2006.01)
*G01N 33/00* (2006.01)
*C12N 15/00* (2006.01)

(52) U.S. Cl. .................. 800/18; 800/3; 800/9; 800/13; 800/14; 800/21; 800/22; 435/455; 435/463; 435/320.1; 435/325

(58) Field of Classification Search .................. 800/3, 800/18, 21, 22, 26, 9, 13, 14; 435/455, 463, 435/320.1, 325
See application file for complete search history.

(56) References Cited

U.S. PATENT DOCUMENTS

| | | | |
|---|---|---|---|
| 5,387,742 A | 2/1995 | Cordell | |
| 5,602,309 A | 2/1997 | Albers et al. | |
| 5,612,486 A | 3/1997 | McConlogue | |
| 5,672,805 A | 9/1997 | Neve | |
| 5,720,936 A | 2/1998 | Wadsworth et al. | |
| 5,767,337 A | 6/1998 | Roses et al. | |
| 5,777,194 A | 7/1998 | Scott et al. | |
| 6,046,381 A * | 4/2000 | Mucke et al. | 800/18 |

OTHER PUBLICATIONS

Moreadith et al., J. Mol. Med., 1997.*
Mullins et al. Journal of Clinical Investigation, 1996.*
Pera et al. Journal of Cell Science 113: 5-10 (2000).*
Raffai et al. Circulation, 102(18), Supplement: 11.150, Abstract (Oct. 31, 2000).*
Baum et al. (2000) *Microsc. Res. Tech.* 50(4):278-281.
Dong and Weisgraber (1996)*J. Biol. Chem.* 271:19053-19057.
Dong et al. (1994) *J. Biol. Chem.* 269:22358-22365.
Weisgraber (1994) *Adv. Protein Chem.* 45:249-302.
Raffai, R. et al, "Hypomorphic Apolipoprotein E Mice", The Journal of Biological Chemistry, Mar. 2002, vol. 277, No. 13, pp. 11064-11068.
Capecchi, M.R. "Targeted Gene Replacement", Scientific American, Mar. 1994, vol. 270, No. 3, pp. 34-41.
Sambrook, J. et al. Molecular Cloning A Laboratory Manual, Second Edition. Cold Spring Harbour Laboratory Press. 1989, pp. 15.3-15.52 and 15.63-15.67.
Plump A.S. et al., "Severe Hypercholesterolemia and Atherosclerosis in Apolipoprotein E-Deficient Mice Created by Homologous Recombination In ES Cells" Cell, Cell Press, Cambridge, NA, US, Vo. 71, Oct. 16, 1992, pp. 343-353.
Ree van J.H. et al., "Inactivation of Apoe and Apoc1 by Two Consecutive Rounds of Gene Targeting: Effects on mRNA Expression Levels of Gene Cluster Members" Human Molecular Genetics, Oxford University Press, Surrey, GB, vol. 4, No. 8, Aug. 8, 1995, pp. 1403-1409.
Knouff, Christopher et al., "Apo E structure determines VLDL clearance and atherosclerosis risk in mice" Journal of Clinical Investigation, vol. 103, No. 11, Jun. 1999, pp. 1579-1586.

(Continued)

*Primary Examiner*—Anne-Marie Falk
*Assistant Examiner*—Thaian N. Ton
(74) *Attorney, Agent, or Firm*—Paula A. Borden; Bret E. Field; Bozicevic Field & Francis LLP

(57) ABSTRACT

The invention provides gene-targeted non-human animals comprising a genetically modified apoE gene encodes a recombinant apoE polypeptide displaying domain interaction. The invention further provides cells isolated from the gene-targeted animals, which cells produce a recombinant apoE polypeptide displaying domain interaction. The invention further provides methods of identifying agents that reduce apoE4 domain interaction, and which are useful to treat apoE4-related neurological and cardiovascular disorders.

6 Claims, 6 Drawing Sheets

OTHER PUBLICATIONS

Hamanaka, Hiroki et al., "Altered cholesterol metabolism in human apolipoprotein E4 knock-in mice" Human Molecular Genetics, vol. 9, No. 3, Feb. 12, 2000, pp. 353-362.

Piedrahita J.A. et al., "Generation of Mice Carrying a Mutant Apolipoprotein E Gene Inactivated by Gene Targeting In Embryonic Stem Cells", Proceedings of the National Academy of Sciences of the United States of America, vol. 89, No. 10, 1992, pp. 4471-4475.

Raffai, et al., Introduction of human apolipoprotein E4 domain Interaction Into mouse apolipoprotein E Proceedings of the National Academy of Sciences of USA, National Academy of Science, Washington, US, vol. 98, No. 20, Sep. 25, 2001, pp. 11587-11591.

* cited by examiner

FIG. 5A

```
HU     KVEQAVETEPEPELRQQTEWQSGQRWELALGRFWDYLRWVQTLSEQVQEE  50
Ba        P  P    DV   A        P
CynM      P  P T      A G       P
Rt     -------- G L  VTD LPG  D P   Q  N              D
Mo     --------- G   VTD L    N P   Q  N              D
GP     ------DV    V V EPAV     P     S               D
Rb     ------    Q V  VPE AR KA  P                 S  D
Cow    DM GELGP -  LTT  PRGKDS P  Q                   D
Dog*      Q EL P --------AG   T  P A  A               D     G
SeaL   EL   E  P --------AG   A  P    A               D

HU     LLSSQVTQELRALMDETMKELKAYKSELEEQLTPVAEETRARLSKELQAA 100
Ba         P        TT                 S
CynM       P        TT                 S
Rt       Q         TV  ED  T V    K     G             A   V   T
Mo       Q          T  ED  T V    K     G                 G V
GP          N      TL IED    V D  A  KE G       D K       A
Rb                 TM  E       V          S M Q           V
Cow       NT  I     T   E      V     E  G  GM Q  Q        V
Dog    V  NT        T          V     A  D  G MTS  Q       VA
SeaL   V  N        TT   E      I    RA     G M S  Q       VA

HU     QARLGADMEDVRGRLVQYRGEVQAMLGQSTEELRVRLASHLRKLRKRLLR 150
Ba              S         S                A
CynM            S         S                A
Rt             L N    G  N  NT             S  ST     M    M
Mo             L N    G  N  HT             A  ST     M    M
GP              E N  'S  S          S      A   T   P M    Q
Rb        E        CN A     A              A  FS
Cow          S     LC A  S                 A   M        P
Dog       R        N  T     L         S    A   F   M      V
SeaL      RS        T S                    A   F   M      V

HU     DADDLQKRLAVYQAGAREGAERGLSAIRERLGPLVEQGRVRAATVGSLAG 200
Ba                         V                              S
CynM                        V                             S
Rt              K     Q     V              Q T  NL AG  A
Mo        E     K           V              Q T  NL AG  A
GP     I E    M K     Q     V        S I     LQ -----  TS
Rb        E     M   G       V                 L   L    ST
Cow          K         S    S         F        QS      LST
Dog       E R   K V       SV S         W    L A  EN K  A    T
SeaL        E       R V   SV T         W    L A  TH K DA    T
```

FIG. 5B

```
HU      QPLQERAQAWGERLRARMEEMGSRTRDRLDEVKEQVAEVRAKLEEQAQQI  250
Ba              L
CynM            L
Rt         RD      LSD I  G L   V  NQA        E   R   ME     S M      T
Mo         RD      F D I  G L   V  NQA        E   R  HME     S M      T
GP                    QM G L  KV    QA        E   R   ME       V V    ---
Rb          R           GHL  V      A         E   R    E       V V    A M
Cow         L    E   RQK HG L  V V AQ           KIRQ  LE     H V      GN M
Dog         L    D     QQ    GQL    S    A GH E  MR   IQ       V M    D
SeaL        R    VN L  QQ    G L    V    A SH    R    ME       Q M    N M

HU      RLQAEAFQARLKSWFEPLVEDMQRQWAGLVEKVQAAVGTSAAPVPSDNH  299
Ba       S                                         A T
CynM     S                                         A T      I
Rt            I      I G               N M   I   S A NSIASTTVPLENQ
Mo            I        G       I   H   N M   I   S A NPIIT  VAQ-ENQ
GP       ----G             MM      R   N IQ      V   A TS-A    QEP
Rb                                             L   MPSK PAAAPIENQ
Cow                 R                            L LRP PTSP    E
Dog      QK                    L       D          A IPTSKPVEEP
SeaL     Q              G                  V              PTTP VETK
```

GENE-TARGETED ANIMAL MODEL OF APOLIPOPROTEIN E4 DOMAIN INTERACTION AND USES THEREOF

CROSS REFERENCE

This application claims the benefit of U.S. Provisional Patent Application Ser. No. 60/276,861, filed Mar. 16, 2001, which is incorporated herein by reference in its entirety.

GOVERNMENT RIGHTS

This invention was made with government support under grant number 2PO1 HL47660 from the National Institutes of Health. The United States Government may have certain rights in this invention.

FIELD OF THE INVENTION

The invention relates generally to the field of genetically altered mice, altered with respect to the expression of apolipoprotein E (apoE) and to assays for determining the effects of compounds on apoE4 domain interaction.

BACKGROUND OF THE INVENTION

Alzheimer's Disease (AD) is a progressive, neurodegenerative disease characterized by cognitive and behavioral changes which include: (a) memory loss; (b) language deterioration; (c) impaired visual-spatial skills; (d) poor judgment; (e) indifferent attitude and (f) aimless, unpredictable behavior. Although AD usually begins after age 60, its onset may occur as early as age 40. AD first appears as memory decline. As the disease progresses over several years, cognition, personality, and the ability to function are all impaired or destroyed. Confusion and restlessness may also occur. The type, severity, sequence, and progression of mental changes vary widely among AD patients. Some people have the disease for only the last 5 years of life, while others may have it for as many as 20 years. The most common cause of death in AD patients is infection.

There is no known etiology or cure for AD and no way to slow the progression of the disease. For some people in the early or middle stages of the disease, medication such as tacrine may alleviate some cognitive symptoms. Also, some medications may help control behavioral symptoms such as sleeplessness, agitation, wandering, anxiety, and depression. These treatments are aimed solely at making the patient more comfortable and do nothing to slow the progression of the underlying disease.

As such, there is much ongoing research that is aimed at the identification and development of new therapeutic agents which can at least slow, if not reverse, the progression of AD. An important step in the identification of therapeutic agents for AD would be the development of a non-human animal model of the disease, as such an animal model would serve as an invaluable tool for screening and testing potential therapeutic agents.

The only non-human animals that naturally develop AD pathological features are aged non-human primates. However, primates are expensive, difficult to use, and require a significant period of time prior to developing AD. These factors make the use of primates as AD animal models prohibitive.

Apolipoprotein E (apoE) is a 34,000 molecular weight protein which is the product of a single gene on chromosome 19. Human ApoE exists in three major isoforms designated apoE2, apoE3 and apoE4. The different isoforms result from amino acid substitutions at amino acid residue positions 112 and 158. The common isoform, apoE3, has a cysteine residue at position 112 and an arginine residue at position 158. The apoE4 isoform differs from apoE3 only at position 112, which is an arginine residue. The apoE4 isoform has been associated with neurological disorders such as AD, with poor outcome following stroke or traumatic head injury, accelerated progression of multiple sclerosis, and with certain cardiovascular disorders.

Human apoE4 exhibits domain interaction due to the presence of an Arg-112, together with an Arg-61 and a Glu-255, the latter two amino acids forming a salt bridge. ApoE4 domain interaction is predicted to represent a key factor responsible for its association with both heart disease and neurological disorders. Like many non-human animals, mouse apoE contains the equivalent of Arg-112 and Glu-255, but lacks the critical Arg-61 required for domain interaction; instead, mouse apoE, as well as apoE of at least nine other species, contains Thr-61. Weisgraber (1994) *Adv. Protein Chem.* 45:249–302.

ApoE contains two structural domains: an amino-terminal and a carboxyl-terminal domain. Weisgraber (1994) *Adv. Protein Chem.* 45:249–302. Each domain is associated with a specific function. The amino terminal domain contains the lipoprotein receptor binding region and the carboxy-terminal domain contains the major lipid-binding elements. The two domains interact with each other in an isoform-specific manner such that amino acid substitutions in one domain influence the function of the other domain, a phenomenon referred to as domain interaction.

Domain interaction is responsible for the preference of apoE4 for very low density lipoproteins (VLDL) contrasted with the preference of apoE3 for high density lipoproteins (HDL). The specific amino acid residues in apoE4 that are involved in this interaction have been identified: arginine-61 in the amino-terminal domain and glutamic acid-255 in the carboxyl-terminal domain. Dong et al. (1994) *J. Biol. Chem.* 269:22358–22365; and Dong and Weisgraber (1996) *J. Biol. Chem.* 271:19053–19057. In addition to differences in lipoprotein preference, apoE4 differs from apoE3 in its interaction with other proteins. For example, tau, a protein found in neurofibrillary tangles, interacts in vitro with apoE3, but not with apoE4.

ApoE4 transgenic animals expressing human apoE isoforms have been reported, including transgenic mice in which the endogenous mouse apoE gene is ablated or inactivated, and gene-targeted mice in which a human apoE coding sequences is stably integrated into the mouse apoE locus. See, e.g., U.S. Pat. Nos. 6,046,381; and 5,767,337. In the transgenic animal models, the human apoE-encoding transgene is under transcriptional control of control elements that are part of the transgene. Furthermore, the transgene inserts at essentially random sites in the genome. Although in the gene-targeted mice, expression of apoE is under the control of endogenous control elements that normally control apoE gene expression, such as tissue-specific elements and promoter elements, there is a potential for species effects.

In view of the foregoing, there is a need in the art for improved animal models of human apoE4 activity. The present invention addresses this need.

Literature

U.S. Pat. Nos. 5,767,337 and 6,046,381 relate to transgenic mice expressing human apoE4. U.S. Patent disclosing other transgenic AD animal models include: U.S. Pat. Nos.

5,777,194; 5,720,936; 5,672,805; 5,612,486; 5,602,309; and 5,387,742. Dong and Weisgraber (1996) *J. Biol. Chem.* 271:19053–19057; and Dong et al. (1994) *J. Biol. Chem.* 269:22358–22365 relate to apoE4 domain interaction. Baum et al. (2000) *Microsc. Res. Tech.* 50(4):278–281 review apoE isoforms in Alzheimer's disease pathology and etiology.

SUMMARY OF THE INVENTION

The present invention provides non-human gene-targeted animal models for the study of apolipoprotein E4-associated pathologies, wherein the endogenous apoE gene of the gene-targeted animal is genetically altered such that the encoded recombinant apoE polypeptide exhibits domain interaction. Since domain interaction is a hallmark of human apoE4, the non-human gene-targeted animals of the instant invention serve as models for human apoE4 domain interaction. The invention further provides cells isolated from a non-human gene-targeted animal of the invention, in particular, cells that produce recombinant apoE exhibiting domain interaction. The invention further provides isolated recombinant apoE protein produced by a cell of the invention. The non-human gene-targeted animals of the invention, as well as cells isolated from such animals and recombinant apoE protein produced by such cells, are useful for screening candidate agents for their ability to reduce apoE domain interaction in the recombinant apoE polypeptide. Such agents are useful for reducing apoE4 domain interaction in human cells producing apoE4, and are therefore useful for treating apoE4-related neurological and cardiovascular disorders.

The invention further provides methods of identifying agents that reduce apoE4 domain interaction. The methods generally comprise contacting a non-human gene-targeted animal (or a cell or a recombinant apoE protein) of the invention with a test agent, and determining the effect, if any, of the test agent on domain interaction, or a phenomenon associated with apoE4 domain interaction. In some embodiments, phenomena associated with apoE4 domain interaction are associated with neurological disorders. The phenomena measured include behavioral phenomena and physiological phenomena. Behavioral phenomena may include cognitive function, such as spatial learning. Physiological phenomena may include the presence of neurofibrillary tangles and Aβ deposits. Alternatively, or in conjunction, the phenomena examined may be examining phenotypes such as neurodegeneration, including neurodegeneration that is age-dependent. In other embodiments, phenomena and/or disorders associated with apoE4 domain interaction are cardiovascular disorders. In these embodiments, phenomena include hyperlipidemia and associated disorders such as coronary artery disease and atherosclerosis.

A primary object of the invention is to provide a method of using a gene-targeted animal model for identifying candidate agents (e.g., a small molecule drug or an endogenous factor) that reduce apoE4 domain interaction and, in doing so, treat disorders related to the presence of apoE4, e.g., neurodegenerative disorders and cardiovascular disorders. Such methods are useful for screening candidate agents for use in treating or relieving the symptoms of apoE4-related pathologies. The cells derived therefrom are also useful for screening biologically active agents that reduce apoE4 domain interaction.

A feature of the invention is that a gene-targeted mouse of the invention expresses a form of apoE that differs from the endogenous apoE in that it exhibits domain interaction. The genetically modified apoE gene of gene-targeted non-human animals of the invention is in its normal genomic environment, and therefore is under control and regulation of the same enhancer and tissue-specific elements that direct expression of the wild-type apoE gene. Thus, an advantage of a gene-targeted non-human animal of the instant invention is that the genetically modified apoE gene is under control of the same elements that control the apoE gene in a wild-type animal of the same species, such that the genetically altered endogenous apoE exhibits wild-type expression patterns. Thus, gene-targeted animals of the invention provide animal models that are representative of human apoE4 in its native environment.

FEATURES OF THE INVENTION

In one aspect, the invention provides a gene-targeted non-human animal comprising a modified endogenous apoE allele, wherein said modified endogenous apoE allele is under transcriptional control of endogenous regulatory elements, and wherein the modified apoE allele encodes a recombinant apoE polypeptide that exhibits domain interaction characteristic of human apoE4.

In another aspect, the invention provides a gene-targeted non-human animal comprising a modified endogenous apoE allele, wherein said modified endogenous apoE allele is under transcriptional control of endogenous regulatory elements, and wherein the modified apoE allele comprises a Thr→Arg substitution at a position equivalent to amino acid 61 of human apoE4.

In another aspect, the invention provides a gene-targeted mouse comprising a modified endogenous mouse apoE allele, wherein said modified endogenous mouse apoE allele is under transcriptional control of endogenous regulatory elements, and wherein the modified mouse apoE allele comprises a Thr→Arg substitution at a position equivalent to amino acid 61 of human apoE4. In some aspects, the gene-targeted mouse is homozygous for the modified endogenous apoE allele.

In another aspect, the invention provides an isolated non-human cell comprising a modified endogenous apoE allele, wherein said modified endogenous apoE allele is under transcriptional control of endogenous regulatory elements, and wherein the modified endogenous apoE allele encodes a recombinant apoE polypeptide that exhibits domain interaction characteristic of human apoE4.

In another aspect, the invention provides an isolated non-human cell comprising a modified endogenous apoE allele, wherein said modified endogenous apoE allele is under transcriptional control of endogenous regulatory elements, and wherein the modified endogenous apoE allele comprises a Thr→Arg substitution at a position equivalent to amino acid 61 of human apoE4.

In another aspect, the invention provides an isolated mouse cell comprising a modified endogenous mouse apoE nucleic acid molecule, wherein said modified endogenous mouse apoE nucleic acid molecule is under transcriptional control of endogenous regulatory elements, and wherein the modified mouse apoE nucleic acid comprises a Thr→Arg substitution at a position equivalent to amino acid 61 of human apoE4.

In another aspect, the invention provides an isolated nucleic acid molecule comprising a nucleotide sequence derived from a non-human apoE gene, which nucleotide sequence is modified such that it encodes an apoE protein that exhibits domain interaction characteristic of human apoE4. In another aspect, the invention provides a recombinant vector comprising such a nucleic acid molecule. In another aspect, the invention provides a recombinant host cell comprising such a recombinant vector.

In another aspect, the invention provides an isolated nucleic acid molecule comprising a nucleotide sequence derived from a non-human apoE gene, which nucleotide sequence is modified such that it comprises a Thr→Arg substitution at a position equivalent to amino acid 61 of human apoE4, and encodes an apoE protein that exhibits domain interaction characteristic of human apoE4. In another aspect, the invention provides a recombinant vector comprising such a nucleic acid molecule. In another aspect, the invention provides a recombinant host cell comprising such a recombinant vector.

In another aspect, the invention provides a recombinant apoE protein encoded by a nucleic acid molecule comprising a nucleotide sequence derived from a non-human apoE gene, which nucleotide sequence is modified such that it encodes an apoE protein that exhibits domain interaction characteristic of human apoE4.

In another aspect, the invention provides a method of identifying an agent for treating an apoE-associated neurological disorder, comprising: contacting the gene-targeted mouse of the invention with a test agent; and b) determining the effect of the test agent on apoE4 activity. In some aspects, the apoE4 activity tested is apoE4 domain interaction.

In another aspect, the invention provides a method of identifying an agent that reduces a phenomenon associated with Alzheimer's disease (AD), comprising: contacting the gene-targeted mouse of the invention with a test agent; and b) determining the effect of the test agent on a phenomenon associated with AD. In some of these aspects, the phenomenon associated with AD is selected from the group consisting of amyloid deposits, neuronal cell loss, and neurofibrillary tangles.

In another aspect, the invention provides a method of identifying an agent that reduces serum cholesterol levels in an individual, comprising: contacting the gene-targeted mouse of the invention with a test agent; and b) determining the effect of the test agent on a serum cholesterol level in the mouse.

In another aspect, the invention provides a method of identifying an agent for reducing the risk of coronary artery disease, comprising: contacting the gene-targeted mouse of the invention with a test agent; and determining the effect, if any, on plaque deposition on a wall of a coronary artery.

In another aspect, the invention provides method of identifying an agent that reduces apoE4 domain interaction, comprising: contacting a recombinant apoE protein of the invention with a test agent; and determining the effect, if any, on an apoE4-associated activity. In some of these aspects, the determination is by an emulsion binding assay.

BRIEF DESCRIPTION OF THE DRAWINGS

FIGS. 5A and 5B depict a comparison of amino acid sequences of apolipoprotein E from 10 species.

DETAILED DESCRIPTION OF THE INVENTION

Figure 1:
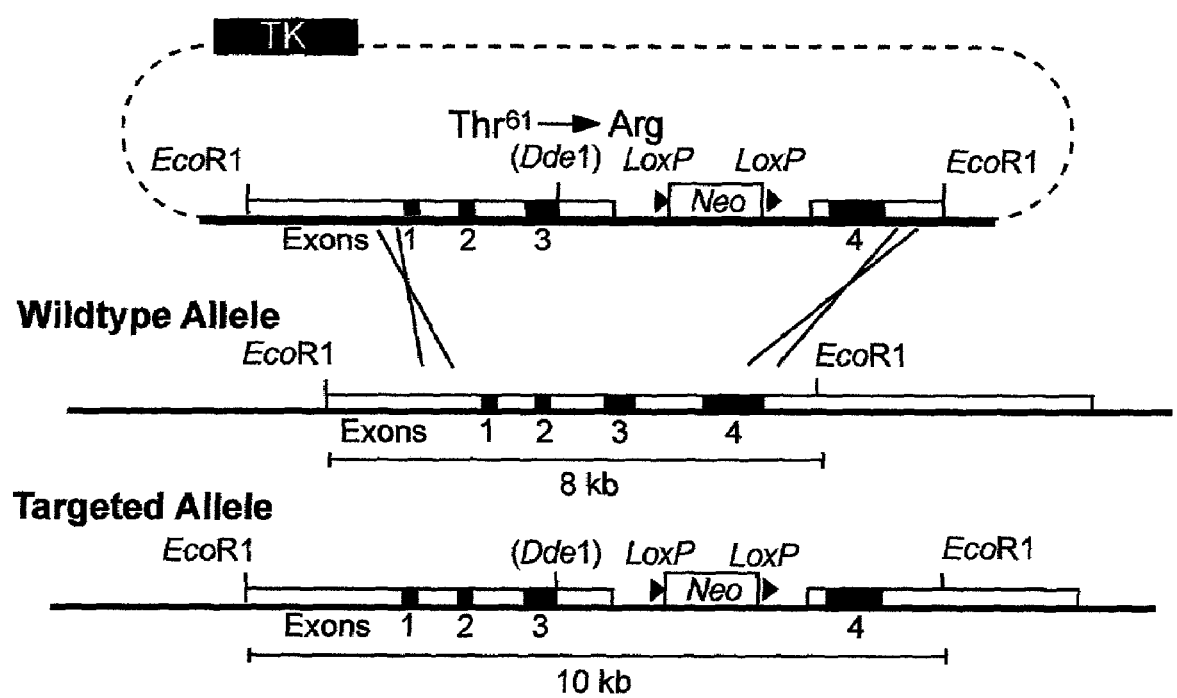
FIG. 1 is a schematic depiction of the gene-targeting vector used to generate an Arg-61 gene-targeted mouse.

Non-human gene-targeted animal models useful for screening drugs or candidate drugs are provided. The animals have a genetically altered endogenous apolipoprotein E gene, such that the encoded recombinant apoE exhibits domain interaction as does human apoE4. In contrast to previous gene-targeted animal models, the genetically altered apoE gene in gene-targeted animals of the present invention is under endogenous transcriptional control and tissue-specific expression. Thus, the genetically altered endogenous apoE gene is expressed in a normal manner, i.e., developmental, tissue-specific, and temporal (e.g., age-dependent) expression are the same as with the wild-type apoE gene, and any species-specific effects seen with previous apoE gene-targeted animals are avoided.

The subject animals are useful for identifying agents that reduce apoE4 domain interaction, and therefore modulate human apoE4 activity. Completely selective compounds will interact with apoE4 selectively, and thus will affect only the apoE4 isoform. In addition, these animals provide a useful model for the behavioral testing of candidate compounds. The animals are useful for testing the efficacy of drugs that reduce apoE4 interaction in treating apoE4-related neurodegenerative disorders and apoE4-associated cardiovascular disorders.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a non-human gene-targeted animal" includes a plurality of such animals and reference to "the apoE gene" includes reference to one or more apoE genes and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

As used herein, the term "endogenous apoE gene" refers to the endogenous apoE gene of the non-human animal which is to be genetically modified; the term "genetically modified endogenous apoE gene" refers to the endogenous apoE gene in the non-human gene-targeted animal which gene is genetically modified to contain an Arg-61 such that the apoE protein encoded thereby exhibits domain interaction; and the term "recombinant apoE polypeptide" refers to the apoE polypeptide encoded by the genetically modified apoE gene, which polypeptide exhibits domain interaction.

The term "transgene" is used herein to describe genetic material which has been or is about to be artificially inserted into the genome of a cell, particularly a mammalian cell for implantation into a living animal.

By "Alzheimer's disease" (abbreviated herein as "AD") is meant a condition associated with formation of neuritic plaques comprising amyloid Aβ protein primarily in the hippocampus and cerebral cortex, as well as impairment in both learning and memory. "AD" as used herein is meant to encompass both AD as well as AD-type pathologies, i.e., diseases of the central nervous system with symptoms similar to AD.

By "symptoms similar to AD" and "phenomenon associated with AD" is meant a structural, molecular, or functional event associated with AD, particularly such an event that is readily assessable in an animal model. Such events include, but are not limited to, amyloid deposition, neuropathological developments, neurofibrillary tangles, learning and memory deficits, and other AD-associated characteristics.

By "Aβ amyloid deposit" is meant a deposit in the brain composed of Aβ amyloid as well as other substances.

By "transformation" is meant a permanent or transient genetic change, preferably a permanent genetic change, induced in a cell following incorporation of new DNA (i.e., DNA exogenous to the cell). Where the cell is a mammalian cell, a permanent genetic change is generally achieved by introduction of the DNA into the genome of the cell.

By "gene-targeted animal" is meant a non-human animal, usually a mammal (e.g., mouse, rat, rabbit, hamster, non-human primate, etc.), having a genetically altered endogenous apoE in the same genomic location as the wild-type (not genetically altered) apoE gene, i.e., the counterpart endogenous apoE gene in a wild-type animal of the same species. Heterologous nucleic acid (i.e., nucleic acid not normally associated with an apoE gene of the species of animal into which the heterologous nucleic acid is introduced) replaces a portion of the endogenous apoE gene in the germ line of such gene-targeted animals by genetic manipulation of, for example, embryos or embryonic stem cells of the host animal.

As used herein, an "apoE4-associated disorder" is any disorder that is caused by the presence of apoE4 in a cell, in the serum, in the interstitial fluid, in the cerebrospinal fluid, or in any other bodily fluid of an individual; any physiological process or metabolic event that is influenced by apoE4 domain interaction; any disorder that is characterized by the presence of apoE4; a symptom of a disorder that is caused by the presence of apoE4 in a cell or in a bodily fluid; a phenomenon associated with a disorder caused by the presence in a cell or in a bodily fluid of apoE4; and the sequelae of any disorder that is caused by the presence of apoE4. ApoE4-associated disorders include apoE4-associated neurological disorders and disorders related to high serum lipid levels. ApoE4-associated neurological disorders include, but are not limited to, sporadic Alzheimer's disease; familial Alzheimer's disease; poor outcome following a stroke; poor outcome following traumatic head injury; and cerebral ischemia. Phenomena associated with apoE4-associated neurological disorders include, but are not limited to, neurofibrillary tangles; amyloid deposits; memory loss; and a reduction in cognitive function. ApoE4-related disorders associated with high serum lipid levels include, but are not limited to, atherosclerosis, and coronary artery disease. Phenomena associated with such apoE4-associated disorders include high serum cholesterol levels.

As used herein, an "apoE4-associated activity" is any activity that is associated with human apoE4, but not with other human apoE isoforms.

As used herein, the terms "determining," "measuring," and "assessing," and "assaying" are used interchangeably and include both quantitative and qualitative determinations.

The terms "polynucleotide" and "nucleic acid molecule" are used interchangeably herein to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes single-, double-stranded and triple helical molecules. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as oligomers or oligos and may be isolated from genes, or chemically synthesized by methods known in the art.

The following are non-limiting embodiments of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A nucleic acid molecule may also comprise modified nucleic acid molecules, such as methylated nucleic acid molecules and nucleic acid molecule analogs. Analogs of purines and pyrimidines are known in the art. Nucleic acids may be naturally occurring, e.g. DNA or RNA, or may be synthetic analogs, as known in the art. Such analogs may be preferred for use as probes because of superior stability under assay conditions. Modifications in the native structure, including alterations in the backbone, sugars or heterocyclic bases, have been shown to increase intracellular stability and binding affinity.

Hybridization reactions can be performed under conditions of different "stringency". Conditions that increase stringency of a hybridization reaction of widely known and published in the art. See, for example, Sambrook et al. (1989). Examples of relevant conditions include (in order of increasing stringency): incubation temperatures of 25° C., 37° C., 50° C. and 68° C.; buffer concentrations of 10×SSC, 6×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water. Examples of stringent conditions are hybridization and washing at 50°C or higher and in 0.1×SSC (9 mM NaCl/0.9 mM sodium citrate).

"$T_m$" is the temperature in degrees Celsius at which 50% of a polynucleotide duplex made of complementary strands hydrogen bonded in anti-parallel direction by Watson-Crick base pairing dissociates into single strands under conditions of the experiment. $T_m$ may be predicted according to a standard formula, such as:

$$T_m=81.5+16.6 \log[X^+]+0.41(\% \text{ G/C})-0.61(\% \text{ F})-600/L$$

where [X$^+$] is the cation concentration (usually sodium ion, Na$^+$) in mol/L; (% G/C) is the number of G and C residues as a percentage of total residues in the duplex; (% F) is the percent formamide in solution (wt/vol); and L is the number of nucleotides in each strand of the duplex.

A polynucleotide or polypeptide has a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at http://ww.ncbi.nlm.nih.gov/BLAST/. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173–187 (1997). Also, the GAP program using the Needleman and Wunsch alignment method can be utilized to align sequences. See *J. Mol. Biol.* 48: 443–453 (1970)

Of interest is the BestFit program using the local homology algorithm of Smith Waterman (Advances in Applied Mathematics 2: 482–489 (1981) to determine sequence identity. The gap generation penalty will generally range from 1 to 5, usually 2 to 4 and in many embodiments will be 3. The gap extension penalty will generally range from about 0.01 to 0.20 and in many instances will be 0.10. The program has default parameters determined by the sequences inputted to be compared. Preferably, the sequence identity is determined using the default parameters determined by the program. This program is available also from Genetics Computing Group (GCG) package, from Madison, Wis., USA.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

A "substantially isolated" or "isolated" polynucleotide is one that is substantially free of the sequences with which it is associated in nature. By substantially free is meant at least 50%, preferably at least 70%, more preferably at least 80%, and even more preferably at least 90% free of the materials with which it is associated in nature. As used herein, an "isolated" polynucleotide also refers to recombinant polynucleotides, which, by virtue of origin or manipulation: (1) are not associated with all or a portion of a polynucleotide with which it is associated in nature, (2) are linked to a polynucleotide other than that to which it is linked in nature, or (3) does not occur in nature.

The term "host cell" includes an individual cell or cell culture which can be or has been a recipient of any recombinant vector(s) or isolated polynucleotide of the invention. Host cells include progeny of a single host cell, and the progeny may not necessarily be completely identical (in morphology or in total DNA complement) to the original parent cell due to natural, accidental, or deliberate mutation and/or change. A host cell includes cells tranfected or infected in vivo or in vitro with a recombinant vector or a polynucleotide of the invention. A host cell which comprises a recombinant vector of the invention is a "recombinant host cell."

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples.

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," and "patient," used interchangeably herein, refer to a mammal, including, but not limited to, murines, simians, humans, mammalian farm animals, mammalian sport animals, and mammalian pets.

Gene-Targeted Non-Human Animals

The present invention provides gene-targeted non-human animals that comprise a genetically altered endogenous apoE gene, wherein the genetically altered apoE gene encodes a recombinant apoE protein that displays domain interaction characteristic of human apoE4. Typically, the recombinant apoE polypeptide encoded by the genetically modified endogenous apoE gene displays domain interaction such that a salt bridge is formed between an arginine at about amino acid 61 and a glutamic acid at about amino acid 255.

The minimum essential elements for domain interaction are the presence of Arg-112, Arg-61, and Glu-255, or the functional equivalent of the foregoing. Thus, any genetic modification of the endogenous apoE gene that results in formation of a salt bridge between Arg-61 and Glu-255 is suitable for generating a gene-targeted non-human animal of the present invention. The amino acid sequence of apoE from a variety of species examined to date contain a threonine at a position that is equivalent to Arg-61 in humans. Weisgraber (1994) *Adv. Protein Chem.* 45:249–302. Thus, mutation of the Thr-61 to Arg-61 results in a recombinant apoE that, like human apoE4, exhibits domain interaction.

FIGS. 5A and 5B depict a comparison of amino acid sequences of apolipoprotein B from 10 species. Sequences are aligned against human apoE4. Hu, Human (Rall et al. (1982) *J. Biol. Chem.* 257:4171–4178; SEQ ID NO:1); Ba, babbon (Hixson et al. (1988) *Genomics* 2:315–323; SEQ ID NO:2); CynM, cynomolgus monkey (Marotti et al. (1989) *Nucleic Acids Res.* 17:1778; SEQ ID NO:3); Rt, rat (McLean et al. (1983) *J. Biol. Chem.* 258:8993–9000; SEQ ID NO:4); Mo, mouse (Rajavashisth et al. (1985) *Proc. Natl. Acad. Sci. USA* 82:8085–8089; SEQ ID NO:5); GP, guinea pig (Matsushima et al. (1990) *Nucl. Acids Res.* 18:202; SEQ ID NO:6); Rb, rabbit (Lee et al. (1991) *J. Lipid Res.* 32:165–171; SEQ ID NO:7); cow (Chan and Li (1991) *Curr. Opin. Lipidol.* 2:96–103; SEQ ID NO:8); dog (Luo et al. (1989) *J. Lipid Res.* 30:1735–1746; and Weisgraber et al. (1980) *Biochem. Biophys. Res. Commun.* 95:374–380; SEQ ID NO:9); SeaL, sea lion (Davis et al. (1991) *J. Lipid Res.* 32:1013–1023; SEQ ID NO: 10). Blanks indicate identity to human sequence; dashes (-) indicate deletions inserted to maximize homology with the human sequence. One-letter amino acid designations are used. A, alanine; C, cysteine; D, aspartic acid; E, glutamic acid; F, phenylalanine; G, glycine; H, histidine; I, isoleucine; K, lysine; L, leucine; M, methionine; N, asparagine; P, proline; Q, glutamine; S, serine; V, valine; W, tryptophan; Y, tyrosine. *, Dog sequence contains amino-terminal extension: DVQPEPELERELEP (SEQ ID NO: 11); †, SeaL sequence contains amino-terminal extension: DVEPESPLEENLEPEL+EPKR (SEQ ID NO:12 and SEQ ID NO:13, respectively).

In generating a non-human gene-targeted animal of the invention, a transgene is used to transform a cell, meaning that a permanent or transient genetic change, preferably a permanent genetic change, is induced in a cell following incorporation of exogenous DNA. A permanent genetic change is generally achieved by introduction of the DNA into the genome of the cell. Vectors for stable integration include plasmids, retroviruses and other animal viruses, YACs, and the like.

Gene-targeted animals comprise a genetically altered endogenous apoE gene that comprises a heterologous nucleic acid sequence that replaces a portion of the endogenous apoE gene, which heterologous nucleic acid is stably integrated in all or a portion of the cells of the animal, especially in germ cells. Unless otherwise indicated, it will be assumed that a gene-targeted animal comprises stable changes to the germline sequence. During the initial construction of the animal, "chimeras" or "chimeric animals" are generated, in which only a subset of cells have the altered genome. Chimeras are primarily used for breeding purposes in order to generate the desired gene-targeted animal. Animals having a heterozygous alteration are generated by breeding of chimeras. Male and female heterozygotes are typically bred to generate homozygous animals. Of interest are gene-targeted mammals, e.g. cows, pigs, goats, non-human primates, horses, etc., and particularly rodents, e.g. rats, mice, etc.

In the present invention, gene-targeted animals comprise a genetic modification in one or both alleles of the endogenous apoE gene, i.e., gene-targeted animals of the invention include both heterozygotes and homozygotes for the genetically modified apoE gene.

The endogenous apoE gene is a wild-type gene, and is under transcriptional control of endogenous control elements, i.e., control elements that are normally associated with an endogenous apoE gene in a wild-type animal of the same species. Endogenous control elements include enhancers, elements that provide for tissue-specific expression of the endogenous apoE gene, promoter elements, and the like.

Targeting Constructs

The introduced heterologous nucleic acid molecule undergoes homologous recombination with the endogenous apoE gene of the species, and converts the endogenous apoE gene to a recombinant apoE gene that encodes a recombinant apoE polypeptide which exhibits domain interaction. Any modification that results in a recombinant endogenous apoE gene that encodes a recombinant apoE protein that exhibits domain interaction is suitable. In some embodiments, the targeting construct converts the threonine-encoding codon in the endogenous gene that is equivalent to Arg-61 of human apoE4 (referred to herein as the "Thr-61 codon") to a codon encoding arginine. In these embodiments, a targeting construct comprises the exon containing the codon for Thr-61, wherein the codon encoding Thr-61 is mutated to encode arginine, and sufficient flanking sequences to allow homologous recombination to occur with the endogenous apoE gene. The mutated codon may be flanked (i.e., may have additional genomic DNA on the 5' and the 3' side of) by from about 100 nucleotide (nt) to about 10 kb, from about 200 nt to about 8 kb, from about 400 nt to about 4 kb, or from about 500 nt to about 2 kb of genomic DNA. The genomic structure and sequence of the apoE gene of a number of species are known. The equivalent of Arg-61 in the human apoE gene in a number of species is known. See, e.g., Weisgraber (1994) *Adv. Protein Chem.* 45:249–302.

The apoE gene of most species encodes an apoE polypeptide having a threonine at a position equivalent to Arg-61 in human apoE4. Weisgraber (1994) *Adv. Protein Chem.* 45:249–302. As noted above, in addition to Arg-61, an apoE polypeptide should also have an arginine at a position corresponding to Arg-112 in human apoE4, and a glutamic acid at a position corresponding to Glu-255 in human apoE4. If an apoE gene in the species does not contain the equivalents of Arg-112 and Glu-255, the targeting construct can comprise additional modifications of the endogenous gene sequence such that, after homologous recombination, the endogenous apoE gene is modified to comprise codons for the equivalent of Arg-112 and Glu-255. (See Weisgraber, (1994)). If codon(s) in addition to the Thr-61 codon are mutated, sufficient flanking sequences to allow homologous recombination are included in the targeting construct.

Methods for generating mutations are well known in the art; any known method can be used to generate an Arg-61 targeting construct. Examples of protocols for site specific mutagenesis may be found in Gustin et al. (1993) *Biotechniques* 14:22; Barany (1985) *Gene* 37:111–23; Colicelli et al. (1985), *Mol. Gen. Genet.* 199:537–9; and Prentki et al. (1984), *Gene* 29:303–13. Methods for site specific mutagenesis can be found in Sambrook et al., Molecular Cloning: A Laboratory Manual, CSH Press 1989, pp. 15.3–15.108; Weiner, et al., (1993) *Gene* 126:35–41; Sayers et al., (1992) *Biotechniques* 13:592–6; Jones, et al., (1992) *Biotechniques* 12:528–30; Barton et al., (1990) *Nucleic Acids Res* 18:7349–55; Marotti, et al., (1989) *Gene Anal. Tech.* 6:67–70; and Zhu (1989) *Anal Biochem* 177:120–4.

If desired, the introduced mutation can, in addition to changing the codon for Thr-61 to a codon for arginine, provide for a restriction endonuclease recognition sequence not present in the endogenous apoE gene. Such a restriction site can be used to determine whether a cell comprises a genetically modified apoE gene.

In one particular embodiment, a construct as described in Example 1 is used. This construct comprises mouse exons 1–4, which were altered to change the codon for Thr-61 to a codon for arginine. When this construct is used to replace the corresponding portion of the endogenous mouse apoE gene, the Thr-61 of mouse apoE is replaced with Arg-61, and apoE that exhibits apoE4 domain interaction is produced.

Whether a given construct will replace a portion of an endogenous apoE gene such that the apoE polypeptide encoded thereby exhibits domain interaction can be determined before making a gene-targeted animal with the construct. This can be achieved by first introducing the construct into a cell line and selecting for cells in which homologous recombination has occurred. Whether the recombinant apoE produced by these cells exhibits domain interaction can be determined using any known assay, including, e.g., an emulsion binding assay, as described in more detail below DNA constructs for homologous recombination will comprise at least a portion of the apoE gene with the desired genetic modification, and will include regions of homology to the target endogenous apoE locus. Conveniently, markers for positive and negative selection are included. Methods for generating cells having targeted gene modifications through homologous recombination are known in the art. For various techniques for transfecting mammalian cells, see Keown et al. *Methods in Enzymology* 185:527–537 (1990).

Generating a Gene-targeted Animal

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of appropriate growth factors, such as leukemia inhibiting factor (LIF). When ES cells have been transformed, they may be used to produce gene-targeted animals. See U.S. Pat. Nos. 5,387,742; 4,736,866; and 5,565,186; and Larson et al. (2000) *Mol. Ther.* 2:631–639 for methods of making gene-targeted animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected.

The chimeric animals are screened for the presence of the modified apoE gene and males and females having the modification are mated to produce homozygous progeny. If the gene alterations cause lethality at some point in development, tissues or organs can be maintained as allogeneic or congenic grafts or transplants, or in in vitro culture.

Isolated Cells

The invention further provides cells isolated from a gene-targeted animal of the invention, particularly cells that synthesize recombinant apoE that exhibits domain interaction. The isolated cells are useful for testing agents for their ability to reduce apoE4 domain interaction. Cells are isolated using standard procedures. Cell lines may be derived from such isolated cells, and immortalized using standard techniques, e.g., through use of viruses. Of particular interest are cells derived from a gene-targeted animal of the invention that synthesize the recombinant apoE protein. In some embodiments, of particular interest are astrocytes and microglial cells that produce the recombinant apoE protein. In other embodiments, cells derived from a gene-targeted animal of the invention are cells that take up recombinant apoE from their environment and which display a physiological change in response to the recombinant apoE. Such cells include, but are not limited to, neuronal cells, e.g., neuronal cells that display apoE4-mediated neurite outgrowth inhibition.

Recombinant ApoE Protein

The invention further provides recombinant apoE proteins, and compositions comprising a recombinant apoE protein. A recombinant apoE protein of the invention is a non-human apoE protein that has been modified such the recombinant apoE protein exhibits domain interaction characteristic of human apoE4 protein. Recombinant apoE protein of the invention can be used in screening assays to identify agents that disrupt domain interaction in the recombinant apoE polypeptide, which agents are thus useful for treating apoE4-associated disorders in humans.

Recombinant apoE proteins comprise one or more amino acid substitutions compared to the apoE polypeptide encoded by the endogenous apoE gene of the gene-targeted animal from which they are derived. Thus, a recombinant apoE polypeptide comprises the equivalents of human apoE Arg-61, Arg-112, and Glu-255, and, as a result, exhibits domain interaction.

The recombinant apoE protein of the subject invention is typically separated from its source, e.g., the gene-targeted animal, or the cell derived therefrom, that synthesizes the recombinant protein. In certain embodiments, the subject proteins are present in a composition that is enriched for subject protein as compared to its source. For example, purified recombinant apoE proteins are provided, where by purified is meant that the recombinant apoE protein is present in a composition that is substantially free of non-recombinant apoE proteins, where by substantially free is meant that less than 90%, usually less than 60% and more usually less than 50% of the composition is made up of recombinant apoE proteins. The proteins of the subject invention may also be present as an isolate, by which is meant that the protein is substantially free of other proteins and other naturally occurring biologic molecules, such as oligosaccharides, polynucleotides and fragments thereof, and the like, where substantially free in this instance means that less than 70%, usually less than 60% and more usually less than 50% of the composition containing the isolated protein is some other naturally occurring biological molecule. In certain embodiments, the proteins are present in substantially pure form, where by substantially pure form is meant at least 95%, usually at least 97% and more usually at least 99% pure.

A recombinant apoE protein that exhibits domain interaction may have one or more amino acid substitutions, insertions, and deletions compared to the wild-type non-human apoE protein, as long as the protein comprises the equivalents of human apoE Arg-61, Arg-112, and Glu-255, and, as a result, exhibits domain interaction. Accordingly, also provided are recombinant apoE proteins that are substantially identical to the sequence of wild-type non-human apoE polypeptide, where by substantially identical is meant that the protein has an amino acid sequence identity to the sequence of wild-type non-human apoE polypeptide of at least about 75%, at least about 80% at least about 85%, at least about 90%, at least about 95%, or at least about 98%.

The subject proteins and polypeptides may be obtained from a gene-targeted animal of the invention, a cell derived from a gene-targeted animal of the invention, or synthetically produced. The subject proteins may also be derived from synthetic means, e.g. by expressing a recombinant gene encoding protein of interest in a suitable host, as described in greater detail below. Any convenient protein purification procedures may be employed, where suitable protein purification methodologies are described in Guide to Protein Purification, (Deuthser ed.) (Academic Press, 1990). For example, a lysate may prepared from the original source and purified using HPLC, exclusion chromatography, gel electrophoresis, affinity chromatography, and the like.

Nucleic Acid Molecules and Host Cells

The invention further provides nucleic acid molecules comprising a nucleotide sequence that encodes a recombinant apoE protein, as well as host cells comprising the nucleic acid molecules. The subject nucleic acid molecules may be part of a vector ("construct") for use in generating a gene-targeted animal of the invention, as described above. In addition, a nucleic acid molecule of the invention may encode all or part of a recombinant apoE polypeptide of the invention, and as such is useful, as part of an expression vector, in producing recombinant apoE polypeptide.

The instant invention provides a nucleic acid molecule comprising one or more exons and one or more introns of an apoE gene, wherein the apoE gene is a non-human apoE gene, and the apoE gene is modified such that the apoE protein encoded thereby exhibits domain interaction characteristic of human apoE4. In some embodiments, a subject nucleic acid molecule comprises a non-human apoE gene, wherein an exon comprising a codon for Thr-61 (or its equivalent in the apoE gene of the animal to be modified) is modified to encode arginine. The sequences of the apoE gene from a number of species are known and are publicly available. Mouse apoE genomic organization is shown in FIG. 1. The sequence of the mouse apoE gene is found under Genbank accession number D00466. Various primate apoE gene sequences are found under GenBank accession numbers AF200508, AF200507, AF200506, and AH009953 (*Hylobates lar*, or gibbon); AH009952, AF200503, AF200504, and AF200505 (*Pongo pygmaeus*, or orangutan); AH009951, AF200500, AG200501, and AF200502 (*Gorilla gorilla*); AH009950, AF200497, AF200498, AF200499 (*Pan troglodytes*, or chimpanzee). Any of these sequences can be modified such that the encoded recombinant apoE polypeptide exhibits domain interaction, e.g., by modifying the codon for Thr-61 to encode arginine.

In some embodiments, nucleic acids of the invention include the open reading frame encoding all or part of the recombinant apoE polypeptide, one or more introns, may further include adjacent 5' and 3' non-coding nucleotide sequences involved in the regulation of expression, and are generally up to about 10 kb in total length, but possibly longer. The DNA sequences encoding all or part of the recombinant apoE are genomic DNA or a fragment thereof. The recombinant apoE gene may be introduced into an appropriate vector for extrachromosomal maintenance or for integration into the host.

A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence.

The sequence of this 5' region, and further 5' upstream sequences and 3' downstream sequences, may be utilized for promoter elements, including enhancer binding sites, that provide for expression in tissues where apoE is expressed. The tissue specific expression is useful for determining the pattern of expression, and for providing promoters that mimic the native pattern of expression. Naturally occurring polymorphisms in the promoter region are useful for determining natural variations in expression, particularly those that may be associated with disease. Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. *Mol Med* 1:194–205 (1995); Mortlock et al. *Genome Res.* 6:327–33 (1996); and Joulin and Richard-Foy *Eur J Biochem* 232:620–626 (1995).

The regulatory sequences may be used to identify cis acting sequences required for transcriptional or translational regulation of apoE expression, especially in different tissues or stages of development, and to identify cis acting sequences and trans acting factors that regulate or mediate expression. Such transcription or translational control regions may be operably linked to an apoE gene in order to promote expression of wild type or altered apoE or other proteins of interest in cultured cells, or in embryonic, fetal or adult tissues, and for gene therapy.

In other embodiments, a nucleic acid molecule of the invention comprises a cDNA comprising sequences that encode all or part of a recombinant apoE protein of the invention. The nucleic acid compositions used in the subject invention may encode all or a part of the apoE polypeptides as appropriate. Fragments may be obtained of the DNA sequence by chemically synthesizing oligonucleotides in accordance with conventional methods, by restriction enzyme digestion, by PCR amplification, etc. For the most part, DNA fragments will be of at least 15 nt, usually at least 18 nt, more usually at least about 50 nt. Such small DNA fragments are useful as primers for PCR, hybridization screening, etc. Larger DNA fragments, i.e. greater than 100 nt are useful for production of the encoded polypeptide. For use in amplification reactions, such as PCR, a pair of primers will be used.

In some embodiments, a nucleic acid molecule of the invention comprises nucleotide sequences of a mouse genomic apoE gene, modified as described above such that the encoded apoE protein exhibits domain interaction characteristic of human apoE4. In other embodiments, a nucleic acid molecule of the invention comprises the coding regions of a mouse apoE gene, modified as described above such that the encoded apoE protein exhibits domain interaction characteristic of human apoE4 (e.g., a cDNA molecule).

The invention further provides nucleic acid molecules that comprise a nucleotide sequence that encodes a recombinant apoE protein that exhibits domain interaction, wherein the nucleic acid molecules hybridize under stringent hybridization conditions to one of a mouse genomic apoE gene, modified such that the encoded apoE protein exhibits domain interaction characteristic of human apoE4; and the coding region of a mouse apoE gene, modified as described above such that the encoded apoE protein exhibits domain interaction characteristic of human apoE4. Examples of stringent conditions are hybridization and washing at 50° C. or higher and in 0.1×SSC (9 mM NaCl/0.9 mM sodium citrate).

The invention further provides nucleic acid molecules that comprise a nucleotide sequence that encodes a recombinant apoE protein that exhibits domain interaction, wherein the nucleic acid molecules have at least about 75%, at least about 80%, at least about 85%, at least about 90%, at least about 95%, or higher, nucleotide sequence identity with one of a mouse genomic apoE gene, modified such that the encoded apoE protein exhibits domain interaction characteristic of human apoE4; and the coding region of a mouse apoE gene, modified as described above such that the encoded apoE protein exhibits domain interaction characteristic of human apoE4.

Subject nucleic acid molecules may comprise other, non-recombinant apoE nucleic acid molecules ("heterologous nucleic acid molecules") of any length. For example, the subject nucleic acid molecules may be flanked on the 5' and/or 3' ends by heterologous nucleic acid molecules of from about 1 nt to about 10 nt, from about 10 nt to about 20 nt, from about 20 nt to about 50 nt, from about 50 nt to about 100 nt, from about 100 nt to about 250 nt, from about 250 nt to about 500 nt, or from about 500 nt to about 1000 nt, or more in length. For example, when used as a probe to detect nucleic acid molecules capable of hybridizing with the subject nucleic acids, the subject nucleic acid molecules may be flanked by heterologous sequences of any length.

The subject nucleic acid molecules may also be provided as part of a vector, a wide variety of which are known in the art and need not be elaborated upon herein. Vectors include, but are not limited to, plasmids; cosmids; viral vectors; artificial chromosomes (YAC's, BAC's, etc.); mini-chromosomes; and the like. Vectors are amply described in numerous publications well known to those in the art, including, e.g., Short Protocols in Molecular Biology, (1999) F. Ausubel, et al., eds., Wiley & Sons. Vectors may provide for expression of the subject nucleic acids, may provide for propagating the subject nucleic acids, or both.

The subject nucleic acid molecules are isolated and obtained in substantial purity, generally as other than an intact chromosome. Usually, the DNA will be obtained substantially free of other nucleic acid sequences that do not include a sequence or fragment thereof of the subject genes, generally being at least about 50%, usually at least about 90% pure and are typically "recombinant", i.e. flanked by one or more nucleotides with which it is not normally associated on a naturally occurring chromosome.

The subject nucleic acid compositions find use in the preparation of all or a portion of the recombinant apoE polypeptides of the invention, as described above. For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to a gene encoding the subject peptides, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, etc.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, or any of the above-described fragment, and up to the complete open reading frame of the gene. After introduction of the DNA, the cells containing the construct may be selected by means of a selectable marker, the cells expanded and then used for expression.

Proteins and polypeptides may be expressed in prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, particularly mammals, e.g. COS 7 cells, Neuro-2A cells, may be used as the expression host cells. In some situations, it is desirable to express the gene in eukaryotic cells, where the encoded protein will benefit from native folding and post-translational modifications. Small peptides can also be synthesized in the laboratory. Polypeptides that are subsets of the complete sequences of the subject proteins may be used to identify and investigate parts of the protein important for function.

Specific expression systems of interest include bacterial, yeast, insect cell and mammalian cell derived expression systems. A wide variety of such systems are known to those skilled in the art.

Recombinant host cells comprising a subject nucleic acid molecule may serve as a source of recombinant apoE protein of the invention. They may also serve in drug screening assays to identify agents that reduce apoE4 domain interaction.

In some embodiments, of particular interest are mammalian cells that normally produce apoE, and cells that normally take up apoE from their environment. Examples of such cells include neuronal cells, microglial cells, and astrocytes. Immortalized neuronal cells, microglial cells, and astrocytes are also of interest.

Drug Screening Assays

The present invention provides methods for identifying agents that reduce apoE4 domain interaction, using a gene-targeted animal, or isolated cell, or isolated recombinant apoE protein of the invention. In some embodiments, the methods identify agents that reduce a phenomenon associated with an apoE4-associated neurological disorder. In other embodiments, the methods identify agents that treat an apoE4-associated cardiovascular disorder. The methods generally comprise contacting a gene-targeted animal or isolated cell of the invention with a test agent, and determining the effect of the agent on the gene-targeted animal, the isolated cell, or recombinant apoE produced by an isolated cell. Agents that reduce apoE4 domain interaction are identified by a change in an activity associated with apoE4; a phenomenon associated with an apoE4-related neurological disorder; or a phenomenon associated with an apoE4-related cardiovascular disorder. ApoE4-associated activities include, but are not limited to, binding preference of the apolipoprotein for a particular class of lipoprotein; binding to tau protein in vitro and/or in vivo; and binding to Aβ protein.

In some embodiments, the invention provides methods of identifying an agent that reduces apoE domain interaction, comprising contacting a non-human gene-targeted animal of the invention with a test agent, and determining the effect, if any, on an activity or disorder associated with apoE4. In other embodiments, the invention provides methods for identifying an agent useful for treating an apoE4-associated neurological disorder, comprising contacting a non-human gene-targeted animal of the invention with a test agent, and determining the effect, if any, on a phenomenon associated with an apoE4-related neurological disorder.

An effect on apoE4 domain interaction, or any associated phenomenon (e.g., a neurological disorder, a symptom of a neurological disorder, a cardiovascular disorder, a symptom of a cardiovascular disorder), or any apoE4-associated activity, can be determined in comparison to a suitable control. Suitable controls for assays using a gene-targeted animal of the invention include a wild-type animal of the same species contacted with the test agent; and a gene-targeted animal not contacted with the test agent. Suitable controls for assays using a cell isolated from a gene-targeted animal of the invention include a cell not contacted with the test agent; and a cell of the same cell type from a wild-type animal of the same species, which cell is contacted with the test agent. Controls for specificity of the test agent on recombinant apoE polypeptide include controls which assay the effect of the test agent on another human apoE isoform, e.g., human apoE3; and controls which assay an activity of the recombinant apoE protein in the absence of the test agent.

A wide variety of assays may be used for this purpose, including in vivo behavioral studies, physiological analyses (e.g., to measure plaque formation on arterial walls; to measure a parameter associated with cardiac function), isoelectric focusing/western blot assays (as described in the Examples), assays to measure serum lipid levels, emulsion binding assays, immunoassays for protein binding (e.g., binding to tau protein), and the like. Depending on the particular assay, whole animals may be used, or cells derived therefrom, or isolated recombinant apoE protein. Cells may be freshly isolated from an animal, or may be immortalized in culture. Any cell that produces recombinant apoE can be used, or that takes up apoE4 from its environment, e.g., neuronal cells, microglial cells, and astrocytes. Cells of particular interest include neural and brain tissue of gene-targeted animals of the invention. The assays may also measure response to acute injury, i.e. examining the neurite growth, repair and remodelling Compounds which stimulate neurite extension in vivo are likely to promote nerve regeneration or the formation of synaptic connections during neuronal remodeling in both the central and peripheral nervous system.

The term "agent" as used herein describes any molecule, e.g. protein or non-protein organic pharmaceutical, with the capability of affecting any of the biological actions of apoE4. Agents of particular interest are those that reduce apoE4 domain interaction. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, e.g., small organic compounds having a molecular weight of more than 50 and less than about 2,500 daltons. Candidate agents comprise functional groups necessary for structural interaction with proteins, e.g., van der Waals interactions and hydrogen bonding, and may include at least an amine, carbonyl, hydroxyl or carboxyl group, and may include at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. New potential therapeutic agents may also be created using methods such as rational drug design or computer modeling.

Screening may be directed to known pharmacologically active compounds and chemical analogs thereof, or to new agents with unknown properties such as those created through rational drug design. Candidate agents for arresting and/or reversing dementia, neuron remodeling, or recovery from acute insults to the nervous system can be screened for their ability to modulate apoE4 function or phenotypes associated with apoE4. Efficacious candidates can be identified by phenotype, i.e. an arrest or reversal of particular cognitive behaviors in comparison with wild-type animals and a gene-targeted animal of the invention.

Agents that have an effect in an assay method of the invention may be subjected to directed or random and/or directed chemical modifications, such as acylation, alkylation, esterification, amidification, etc. to produce structural analogs. Such structural analogs include those that increase bioavailability, and/or reduced cytotoxicity. Those skilled in the art can readily envision and generate a wide variety of structural analogs, and test them for desired properties such as increased bioavailability and/or reduced cytotoxicity and/or ability to cross the blood-brain barriers.

Screening may also determine if an agent for a different use has an unintended adverse effect on apoE-related functions, including but not limited to neuronal remodeling, repair and recovery from acute insults. For example, certain classes of pharmaceutical agents widely used to treat behavior problems in people with dementia may actually worsen their mental decline. Neuroleptic agents such as chlorpromazine, haloperidol and thioridazine are widely used to treat behavior problems in patients with various forms of dementia, including AD. Recent studies suggest that these drugs may in fact worsen the cognitive or any other function of people treated with these agents. Therapeutic agents such as neuroleptic drugs can be subjected to the methods of the present invention to determine if they are in fact having a detrimental effect on cognitive or any other function by modulation of apolipoprotein E4. This screening can be used for any agent predicted to affect cognitive function to determine if the agent may inadvertently have an unintended effect on apolipoprotein E4 function.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Samples derived from a gene-targeted animal of the invention may also be used in assays. Samples, as used herein, include biological fluids such as tracheal lavage, blood, cerebrospinal fluid, tears, saliva, lymph, dialysis fluid and the like; organ or tissue culture derived fluids; and fluids extracted from physiological tissues. Also included in the term are derivatives and fractions of such fluids. The number of cells in a sample will generally be at least about $10^3$, usually at least $10^4$ more usually at least about $10^5$. The cells may be dissociated, in the case of solid tissues, or tissue sections may be analyzed. Alternatively a lysate of the cells may be prepared.

For example, detection may utilize staining of cells or histological sections, performed in accordance with conventional methods. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

An alternative method depends on the in vitro detection of binding between antibodies and apoE4 in a lysate. Measuring the concentration of binding in a sample or fraction thereof may be accomplished by a variety of specific assays. A conventional sandwich type assay may be used. For example, a sandwich assay may first attach specific antibodies to an insoluble surface or support. The particular manner of binding is not crucial so long as it is compatible with the reagents and overall methods of the invention. They may be bound to the plates covalently or non-covalently, preferably non-covalently.

The insoluble supports may be any compositions to which polypeptides can be bound, which is readily separated from soluble material, and which is otherwise compatible with the overall method. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

A number of assays are known in the art for determining the effect of a drug on animal behavior. Behavioral abnormalities and recovery from acute or chronic injury in animal models are useful for testing the effect, interactions, and specificity of a candidate biologically active agent. Some examples are provided, although it will be understood by one of skill in the art that many other assays may also be used. The subject animals may be used by themselves, or in combination with control animals.

Candidate agents are obtained from a wide variety of sources including libraries of synthetic or natural compounds. For example, numerous means are available for random and directed synthesis of a wide variety of organic compounds and biomolecules, including expression of randomized oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Detection may utilize staining of cells or histological sections, performed in accordance with conventional methods. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

A number of assays are known in the art for determining the effect of a drug on animal behavior and other phenomena associated with neurodegeneration or impairment of cognitive abilities. Some examples are provided, although it will be understood by one of skill in the art that many other assays may also be used. The subject animals may be used by themselves, or in combination with control animals.

The screen using the gene-targeted animals of the invention can employ any phenomena associated learning impairment, dementia or cognitive disorders that can be readily assessed in an animal model. The screening can include assessment of phenomena including, but not limited to: 1) analysis of molecular markers (e.g., levels of expression of recombinant apoE gene products in brain tissue; presence/absence in brain tissue of recombinant apoE; and formation of neurite plaques; formation of Aβ deposits); 2) assessment behavioral symptoms associated with memory and learning; 3) detection of neurodegeneration characterized by progressive and irreversible deafferentation of the limbic system, association neocortex, and basal forebrain (neurodegeneration can be measured by, for example, detection of synaptophysin expression in brain tissue) (see, e.g., Games et al. *Nature* 373:523–7 (1995)). These phenomena may be assessed in the screening assays either singly or in any combination.

Preferably, the screen will include control values (e.g., the level of amyloid production in the test animal in the absence of test compound(s)). Test substances which are considered positive, i.e., likely to be beneficial in the treatment of apoE4-associated disorders, will be those which have a substantial effect upon an apoE4-associated phenomenon (e.g., test agents that are able to rescue behavioral disorders caused by altered expression of apoE).

Methods for assessing these phenomena, and the effects expected of a candidate agent for treatment of apoE4-associated disorders, are known in the art. For example, methods for using gene-targeted animals in various screening assays for, for example, testing compounds for an effect on AD, are found in WO 9640896, published Dec. 19, 1996; WO 9640895, published Dec. 19, 1996; WO 9511994, published May 4, 1995 (describing methods and compositions for in vivo monitoring of Aβ; each of which is incorporated herein by reference with respect to disclosure of methods and compositions for such screening assays and techniques). Examples of assessment of these phenomena are provided below, but are not meant to be limiting.

ApoE4-Associated Activity

Assays include assays for apoE4-associated activity, and include, but are not limited to, a binding preference of apoE4 to particular class of lipoprotein, and binding to tau protein. Such assays typically involve contacting a recombinant apoE protein with a test agent, to form a sample, and determining the effect, if any, of the agent on an apoE4-associated activity.

ApoE4 has a binding preference for VLDL, while apoE3 has a binding preference for HDL. Typically, when plasma lipoproteins are allowed to bind to labeled apoE4 and apoE3, the bound proteins fractionated, and the amount of apoE4 and apoE3 in each fraction measured, the amount of apoE4 in the VLDL, IDL/LDL, and HDL fractions is about 35%, about 23%, about 42%, respectively, while the amount of apoE3 in each of these fractions is about 20%, about 20%, about 60%, respectively. Thus, in some embodiments, an agent that reduces apoE4 domain interaction causes apoE4 to have a binding preference for HDL. Whether apoE4, when contacted with an agent that reduces apoE4 domain interaction, has a binding preference for HDL over VLDL can be determined using any known assay. As one non-limiting example, an assay as described in Dong et al. (1994) *J. Biol. Chem.* 269:22358–22365. For example, samples comprising detectably labeled apoE4 and apoE3 (e.g., labeled with $^{125}$I), are mixed with plasma at about 37° C. for about 2 hours, after which time the samples are fractionated into various lipoprotein classes (e.g., by chromatography), and the amount of label in each fraction is determined.

Emulsion Binding Assays

A non-limiting example of an emulsion binding assay to assess domain interaction is as follows. Triolein (160 mg) and L-alpha-Phosphatidylcholine (40 mg) are combined and dried under nitrogen. After the addition of 8 mls of buffer (10 mM Tris, 100 mM KCl, 1 mM EDTA, pH 8.0), the mixture is sonicated in a water bath to obtain a heterogeneous mix of emulsion particles. The particles are harvested by ultracentrifugation (TLA 100.2 rotor, 30,000 rpm for 30 minutes) and the subsequent lipid cake is removed by tube slicing and resuspended in 100 µl 20 mM Phosphate Buffer (PB). Triolein and phospholipid content are measured and total emulsion particle concentration is determined. Freshly denatured and renatured Apolipoprotein E3 and E4 are radiolabelled using Bolton-Hunter Reagent [$^{125}$I] (ICN). Specific Activity is determined using Lowry method and Gamma 8000 counter. The binding affinity of apoE3 and apoE4 to emulsion particles may be determined as follows. In glass tubes, 25 µg of protein (with iodinated tracer) are reduced with 1% β-mercaptoethanol. Two hundred fifty µg of emulsion particles and 2.5 µl of compound (10 mM stock) are added and the final mixture is brought up to 250 µl with 20 mM phosphate buffer (PB). The reaction mixture is then incubated in a 37° C. water bath for 2 hours before being transferred to 1.5 ml ultracentrifuge tubes. Finally, 50 µl of 60% sucrose is mixed with the sample and 400 µl 20 mM PB is carefully layered on top. Using a TLA 100.2 rotor, the tube is spun at 30,000 rpm for 30 minutes and subsequently cut to separate the floating emulsion particle layer from the free protein at the bottom of the tube. These fractions are then combined with the respective half of the actual tube and counted using a Gamma-8000. From these results, total emulsion-bound protein is compared to total free protein. Control binding assays are conducted without the addition of test compounds to determine recovery and apoE3 and apoE4 respective affinity for emulsion particles.

Binding to Tau Protein

ApoE3 interacts with tau in vitro, while apoE4 does not. In some embodiments, an agent that reduces apoE4 domain interaction causes apoE4 to bind tau in vitro and/or in vivo. Whether a protein binds tau in vitro, e.g., in the presence of an agent that reduces apoE4 domain interaction, can be determined using standard assays for measuring or detecting protein-protein interaction. A non-limiting example of an assay is provided in Strittmatter et al. (1994) *Exp. Neurol.* 125:163–171.

Pathological Studies

After exposure to the candidate agent, the animals are sacrificed and analyzed by immunohistology for either: 1) neuritic plaques and neurofibrillary tangles (NFTs) in the brain and/or 2) levels of recombinant apoE. The brain tissue is fixed (e.g, in 4% paraformladehyde) and sectioned; the sections are stained with antibodies reactive with apoE. Secondary antibodies conjugated with fluorescein, rhodamine, horse radish peroxidase, or alkaline phosphatase are used to detect the primary antibody. These experiments permit identification of amyloid plaques and the regionalization of these plaques to specific areas of the brain.

Sections can also be stained with other diagnostic antibodies recognizing antigens such as Alz-50, tau, A2B5, neurofilaments, neuron-specific enolase, and others that are characteristic of neurodegeneration. Staining with thioflavins and congo red can also be carried out to analyze co-localization of AD deposits within the neuritic plaques and NFTs.

To assess the effect of a test agent on apoE4-related cardiovascular disorders and phenomena associated with such disorders, a gene-targeted animal can be fed a high-cholesterol diet. A gene-targeted animal of the invention fed a high-cholesterol diet can be treated with a test agent, and various parameters measured, including, but not limited to, serum cholesterol levels, total plasma cholesterol levels, total plasma lipoproteins levels, levels of specific plasma lipoproteins (e.g., HDL, LDL, VLDL), and atherosclerosis. Standard assays to measure such parameters are known to those skilled in the art, and any known assay can be used. Serum cholesterol levels in response to the test agent can be measured using standard assays. Development of arterial plaques can be measured using standard assays.

Analysis of Recombinant ApoE Expression 1) mRNA: mRNA can be isolated by the acid guanidinium thiocyanate phenol:chloroform extraction method (Chomczynski et al., *Anal Biochem* 162:156–159 (1987)) from cell lines and tissues of gene-targeted animals to determine expression levels by Northern blots. Whether a recombinant apoE gene is expressed can be determined using, e.g., a labeled oligonucleotide probe that spans the Thr-61 to Arg-61 mutation. The labeled oligonucleotide may comprise the mutation that led to the Arg-61 substitution, in which case expression of the genetically modified gene is identified by hybridization with the labeled probe.

2) In situ Hybridizations: Radioactive or enzymatically labeled probes can be used to detect mRNA in situ. The probes are degraded approximately to 100 nucleotides in length for better penetration of cells. The procedure of Chou et al. *J Psychiatr Res* 24:27–50 (1990) for fixed and paraffin embedded samples is briefly described below although similar procedures can be employed with samples sectioned as frozen material.

Paraffin slides for in situ hybridization are dewaxed in xylene and rehydrated in a graded series of ethanols and finally rinsed in phosphate buffered saline (PBS). The sections are postfixed in fresh 4% paraformaldehyde. The slides are washed with PBS twice for 5 minutes to remove paraformaldehyde. Then the sections are permeabilized by treatment with a 20 mu g/ml proteinase K solution. The sections are refixed in 4% paraformaldehyde, and basic molecules that could give rise to background probe binding are acetylated in a 0.1M triethanolamine, 0.3M acetic anhydride solution for 10 minutes. The slides are washed in PBS, then dehydrated in a graded series of ethanols and air dried. Sections are hybridized with antisense probe, using sense probe as a control. After appropriate washing, bound radioactive probes are detected by autoradiography or enzymatically labeled probes are detected through reaction with the appropriate chromogenic substrates.

3) Western Blot Analysis: Protein fractions can be isolated from tissue homogenenates and cell lysates and subjected to Western blot analysis as described by Harlow et al., *Antibodies: A laboratory manual*, Cold Spring Harbor, N.Y., (1988); Brown et al., *J. Neurochem* 40:299–308 (1983); and Tate-Ostroff et al., *Proc Natl Acad Sci* 86:745–749 (1989)). Only a brief description is given below.

The protein fractions can be denatured in Laemmli sample buffer and electrophoresed on SDS-polyacrylamide gels. The proteins are be then transferred to nitrocellulose filters by electroblotting. The filters are blocked, incubated with primary antibodies, and finally reacted with enzyme conjugated secondary antibodies. Subsequent incubation with the appropriate chromogenic substrate reveals the position of apoE proteins. An antibody that distinguishes between an apoE polypeptide having Thr-61 from one having Arg-61 may be employed.

4) Isoelectric focusing combined with western blot analysis. As a result of the arginine for threonine substitution, a recombinant apoE protein may have a different charge than the wild-type protein. Therefore, isoelectric focusing can be used to distinguish between wild-type and recombinant apoE proteins. Protein fractions are isolated as described above, and subjected to isoelectric focusing, as described in the Examples, using standard techniques. Isoelectric focusing is generally performed using ampholines, typically in a pH range of 4–7, on polyacrylamide gels (or other suitable matrix), in the presence of 6 M urea.

Behavioral Studies of Gene-Targeted Mice and Rats

Behavioral tests designed to assess learning and memory deficits can be employed. An example of such as test is the Morris Water maze (Morris *Learn Motivat* 12:239–260 (1981)). In this procedure, the animal is placed in a circular pool filled with water, with an escape platform submerged just below the surface of the water. A visible marker is placed on the platform so that the animal can find it by navigating toward a proximal visual cue. Alternatively, a more complex form of the test in which there are no formal cues to mark the platform's location will be given to the animals. In this form, the animal must learn the platform's location relative to distal visual cues. Alternatively, or in addition, memory and learning deficits can be studied using a 3 runway panel for working memory impairment (attempts to pass through two incorrect panels of the three panel-gates at four choice points) (Ohno et al. *Pharmacol Biochem Behav* 57:257–261 (1997)).

Studies of Animal Models of Neuronal Damage

Rodent models of neuronal damage, for example neuronal damage caused by cerebral ischemia, may be examined to determine the effect on an agent on apoE4 domain interaction in the extent of neuronal damage caused by traumatic events as well as their role in neuronal remodeling, repair and recovery from such insults. Rodent models of cerebral ischemia, both global ischemia and focal ischemia, are useful for studying mechanisms controlling the occurrence of cerebral ischemia and potential therapeutic strategies for treatment of injury caused by ischemic events. Animal models of global ischemia, which is usually transient, have widely affected brain areas but typically give rise to neuronal alterations in selectively vulnerable brain regions. Examples of such models include, but are not limited to, the two vessel occlusion model of forebrain ischemia, the four vessel occlusion model of forebrain ischemia, and ischemia models involving elevated cerebrospinal fluid pressure. See Ginsberg and Busto, *Stroke,* 20:1627–1642 (1989), which is herein incorporated by reference. Models of focal ischemia may mimic ischemic stroke injury, and typically give rise to localized brain infarction. Examples of models of focal ischemia include, but are not limited to, middle cerebral artery occlusion, photochemically induced focal cerebral thrombosis, blood clot embolization, microsphere embolization and the like. See McAuley, *Cerebrovasc. Brain Metab. Review,* 7:153–180 (1995) which is herein incorporated by reference.

Any of these models may be used in the gene-targeted animals of the present invention to examine the effect of an agent on apoE4 domain interaction, both during traumatic brain injury and in neuronal remodeling and repair following a traumatic ischemic insult to the brain. For example, to examine the effect of a test agent in a rodent stroke model, the rate and nature of injury following cerebral ischemia may be examined using the gene-targeted animals of the present invention. In such rodent models, the trangenic animals can be subjected to an ischemic injury, and the animals monitored for extent of damage and/or recovery following injury. In addition, the effect of the agent may be examined in the neuronal remodeling and recovery of these animal models. The effect of the test agent in these processes may be examined using biochemical, pathological, physiological or behavioral methods, as described in the preceding sections.

Moreover, the effects of different therapies, including the use of therapeutic agents, may be examined to determine potential therapeutic strategies for mitigating and/or reversing the neuronal damage in these animal models. For instance, in a rodent model of focal cerebral ischemia using the animals of the present invention, different candidate therapuetic agents may be administered prior to the induction of the trauma to examine the preventive effect of agents in specific brain regions, and whether that preventive effect is apoE-isoform-dependent. Alternatively, a candidate therapeutic agent may be administered following the induction of the injury to determine the mitigating or recovery effects of that agent, whether the agent is specific to certain brain regions, and if the effect or the specificity of the agent is apoE-isoform dependent.

ApoE4-Related Cardiovascular Disorders

Gene-targeted animals of the invention can be used to screen agents for their ability to treat hyperlipidemia and other apoE4-related cardiovascular disorders.

A gene-targeted animal of the invention can be used to test agents for an effect on serum cholesterol levels. In these embodiments, the methods comprise contacting a gene-targeted animal of the invention with a test agent, and determining the effect, if any, on serum cholesterol level. A reduction in serum cholesterol level, when compared with an effect of the agent on a control animal, indicates that the agent is effective in reducing serum cholesterol levels.

Gene-targeted animals of the invention can also be used to test agents for an effect on a disease associated with hyperlipidemia, e.g., coronary artery disease and atherosclerosis. A gene-targeted animal treated with a test agent can be analyzed for the presence of arterial plaques using standard methods.

Therapeutic Agents

The invention provides agents identified using the methods described herein. Agents that reduce apoE4 domain interaction are used to treat apoE4-related disorders. An effective amount of the active agent is administered to the host, where "effective amount" means a dosage sufficient to produce a desired result. Generally, the desired result is at least a reduction in enzymatic activity of a subject therapeutic agent as compared to a control.

Formulations, Dosages, and Routes of Administration

The invention provides formulations, including pharmaceutical formulations, comprising an agent that reduces apoE4 domain interaction. In general, a formulation comprises an effective amount of an agent that reduces apoE4 domain interaction. An "effective amount" means a dosage sufficient to produce a desired result, e.g., reduction in apoE4 domain interaction, an increase in neurite outgrowth, a reduction in serum lipid levels, a reduced risk of heart disease, etc. Generally, the desired result is at least a reduction in apoE4 domain interaction as compared to a control. An agent that reduces apoE4 domain interaction may delivered in such a manner as to avoid the blood-brain barrier, as described in more detail below. An agent that reduces apoE4 domain interaction may be formulated and/or modified to enable the agent to cross the blood-brain barrier, as described in more detail below.

Formulations

In the subject methods, the active agent(s) may be administered to the host using any convenient means capable of resulting in the desired inhibition of apoE4 domain interaction, reduction in any apoE4-associated neurological disorder, apoE4-associated cardiovascular disorder, reduction in an apoE4-associated activity, etc.

Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

Other modes of administration will also find use with the subject invention. For instance, an agent of the invention can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), preferably about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

An agent of the invention can be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Dosages

Although the dosage used will vary depending on the clinical goals to be achieved, a suitable dosage range is one which provides up to about 1 µg to about 1,000 µg or about 10,000 µg of an agent that reduces apoE4 domain interaction and can be administered in a single dose. Alternatively, a target dosage of an agent that reduces apoE4 domain interaction can be considered to be about in the range of about 0.1–1000 µM, about 0.5–500 µM, about 1–100 µM, or about 5–50 µM in a sample of host blood drawn within the first 24–48 hours after administration of the agent.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

Routes of Administration

An agent that reduces apoE4 domain interaction is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, intratumoral, subcutaneous, intradermal, topical application, intravenous, rectal, nasal, oral and other parenteral routes of administration. Routes of administration may be combined, if desired, or adjusted depending upon the agent and/or the desired effect. The composition can be administered in a single dose or in multiple doses.

The agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

The agent can also be delivered to the subject by enteral administration. Enteral routes of administration include, but are not necessarily limited to, oral and rectal (e.g., using a suppository) delivery.

Methods of administration of the agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as an apoE4-associated neurological disorder and pain associated therewith. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of hosts (wherein the term "host" is used interchangeably herein with the terms "subject" and "patient") are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Kits with unit doses of the active agent, e.g. in oral or injectable doses, are provided. In such kits, in addition to the containers containing the unit doses will be an informational package insert describing the use and attendant benefits of the drugs in treating pathological condition of interest. Preferred compounds and unit doses are those described herein above.

Crossing the Blood-brain Barrier

The blood-brain barrier limits the uptake of many therapeutic agents into the brain and spinal cord from the general circulation. Molecules which cross the blood-brain barrier use two main mechanisms: free diffusion; and facilitated transport. Because of the presence of the blood-brain barrier, attaining beneficial concentrations of a given therapeutic agent in the central nervous system (CNS) may require the use of drug delivery strategies. Delivery of therapeutic agents to the CNS can be achieved by several methods.

One method relies on neurosurgical techniques. In the case of gravely ill patients such as accident victims or those suffering from various forms of dementia, surgical intervention is warranted despite its attendant risks. For instance, therapeutic agents can be delivered by direct physical introduction into the CNS, such as intraventricular or intrathecal injection of drugs. Intraventricular injection may be facilitated by an intraventricular catheter, for example, attached to a reservoir, such as an Ommaya reservoir. Methods of introduction may also be provided by rechargeable or biodegradable devices. Another approach is the disruption of the blood-brain barrier by substances which increase the permeability of the blood-brain barrier. Examples include intra-arterial infusion of poorly diffusible agents such as mannitol, pharmaceuticals which increase cerebrovascular permeability such as etoposide, or vasoactive agents such as leukotrienes. Neuwelt and Rappoport (1984) *Fed. Proc.* 43:214–219; Baba et al. (1991) *J. Cereb. Blood Flow Metab.* 11:638–643; and Gennuso et al. (1993) *Cancer Invest.* 11:638–643.

Further, it may be desirable to administer the pharmaceutical agents locally to the area in need of treatment; this may be achieved by, for example, local infusion during surgery, by injection, by means of a catheter, or by means of an implant, said implant being of a porous, non-porous, or gelatinous material, including membranes, such as silastic membranes, or fibers.

Therapeutic compounds can also be delivered by using pharmacological techniques including chemical modification or screening for an analog which will cross the blood-brain barrier. The compound may be modified to increase the hydrophobicity of the molecule, decrease net charge or molecular weight of the molecule, or modify the molecule, so that it will resemble one normally transported across the blood-brain barrier. Levin (1980) *J. Med. Chem.* 23:682–684; Pardridge (1991) in: *Peptide Drug Delivery to the Brain*; and Kostis et al. (1994) *J. Clin. Pharmacol.* 34:989–996.

Encapsulation of the drug in a hydrophobic environment such as liposomes is also effective in delivering drugs to the CNS. For example WO 91/04014 describes a liposomal delivery system in which the drug is encapsulated within liposomes to which molecules have been added that are normally transported across the blood-brain barrier.

Another method of formulating the drug to pass through the blood-brain barrier is to encapsulate the drug in a cyclodextrin. Any suitable cyclodextrin which passes through the blood-brain barrier may be employed, including, but not limited to, J-cyclodextrin, K-cyclodextrin and derivatives thereof. See generally, U.S. Pat. Nos. 5,017,566, 5,002,935 and 4,983,586. Such compositions may also include a glycerol derivative as described by U.S. Pat. No. 5,153,179.

Delivery may also be obtained by conjugation of a therapeutic agent to a transportable agent to yield a new chimeric transportable therapeutic agent. For example, vasoactive intestinal peptide analog (VIPa) exerted its vasoactive effects only after conjugation to a monoclonal antibody (Mab) to the specific carrier molecule transferrin receptor, which facilitated the uptake of the VIPa-Mab conjugate through the blood-brain barrier. Pardridge (1991); and Bickel et al. (1993) *Proc. Natl. Acad Sci. USA* 90:2618–2622. Several other specific transport systems have been identified, these include, but are not limited to, those for transferring insulin, or insulin-like growth factors I and II. Other suitable, non-specific carriers include, but are not limited to, pyridinium, fatty acids, inositol, cholesterol, and glucose derivatives. Certain prodrugs have been described whereby, upon entering the central nervous system, the drug is cleaved from the carrier to release the active drug. U.S. Pat. No. 5,017,566.

Subjects Suitable for Treatment with a Therapeutic Agent of the Invention

A variety of subjects are suitable for treatment with an agent identified by a method of the invention. Suitable subjects have one or two apoE4 alleles. Suitable subjects include any individual, particularly a human, who has an apoE4-associated disorder, who is at risk for developing an apoE4, who has had an apoE4-associated disorder and is at risk for recurrence of the apoE4-associated disorder, or who is recovering from an apoE4-associated disorder.

Such subjects include, but are not limited to, individuals who have been diagnosed as having Alzheimer's disease; individuals who have suffered one or more strokes; individuals who have suffered traumatic head injury; individuals who have high serum cholesterol levels; individuals who have Aβ deposits in brain tissue; individuals who have had one or more cardiac events; subjects undergoing cardiac surgery; and subjects with multiple sclerosis.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Example 1

Targeting the Mouse Apoe Gene Locus to Introduce Arg-61

The gene-targeting vector that was designed is shown in FIG. 1. Like human Apoe, the mouse gene contains four exons and three introns, contained within an 8-kb EcoR1 fragment. The codon for the Thr-61 equivalent in the mouse gene is located at the end of the third exon, exactly as it is in the human gene. Mutation of the ACG threonine codon to a AGG arginine codon resulted in introduction of a unique Dde1 restriction site, which was used as a diagnostic marker. A thymidine kinase (TK) gene was used as a negative selection marker, and the Neo gene was used as a positive selection marker. The Neo gene was placed within the third intron close to the mutation site to reduce the probability that it would be separated from the mutation during recombination. The Neo gene was flanked with loxP sites (the recognition sequence for the site-specific DNA recombinase, Cre) to allow its removal by Cre-mediated recombination by crossing the gene-targeted mice with Cre transgenic mice (obtained from Dr. Gail Martin, UCSF) carrying the Nes-Cre1 gene, which is active in the germline. Meyers et al. (1998) *Nat. Genet.* 18:136–141. Our strategy was to remove the Neo gene to avoid any complications of its presence.

Embryonic stems (ES) 129 SvJ cells (obtained from the Gladstone Blastocyst Core) were electroporated with the targeting vector and were selected first against TK incorporation and then for neomycin resistance. Targeted cells heterozygous for the recombination event displayed the expected expansion of the mouse locus to 10 kb for the EcoR1 fragment on southern blots and the presence of the Dde1 restriction site. The targeted ES cells were injected into C57B1/6 blastocysts, and the blastocysts were implanted into pseudopregnant female mice. Three chimeric males were obtained, all of which displayed germline transmission of the targeted allele. Southern blot analysis of DNA from heterozygous and homozygous targeted mice before removal of the Neo gene displayed the expected expansion of the apoE locus. The Neo gene was removed by crossing one of the lines with the Nes-Cre1 mice.

Comparison of apoE mRNA tissue distribution. Comparison of apoE mRNA levels in various tissues and organs of wild-type (wt) and homozygous Arg-61 (Neo removed) mice demonstrated that expression was restored in all apoE-expressing tissues and organs, including the brain, by Cre-mediated recombination. Furthermore, the mRNA expression levels in Arg-61 mice were identical to levels in wt mice. These results demonstrate that the pattern and level of expression of the Arg-61 mutant gene was identical to that of the wt gene. Targeted mice have been crossed into the C57B1/6 background to remove the Nes-Cre1 gene.

Arg-61 mice: Proof that domain interaction occurs in vivo. Domain interaction in the mouse Arg-61 mutant apoE was demonstrated using an in vitro lipoprotein binding assay. To demonstrate domain interaction with this mutation in vivo, we analyzed the effect of the Arg-61 mutant apoE on plasma lipoprotein metabolism. The results unequivocally demonstrate that the Arg-61 mice exhibit evidence of domain interaction with effects on plasma lipoprotein metabolism that are consistent with the known behavior of apoE4 in humans. For example, in humans, plasma levels of apoE4 are lower than those of apoE3 and apoE2. Davignon et al. (1988) *Arteriosclerosis* 8:1–21; and Boerwinkle and Utermann (1988) *Am. J. Hum. Genet.* 42:104–112. This is clearly illustrated in the plasma from apoE4/3 heterozygotes using isoelectric focusing. In these subjects, the apoE4 band is reduced compared with that of apoE3 or apoE2. This difference may result from the preference of apoE4 for VLDL, which turns over at a faster rate in plasma than HDL.

Figure 2:
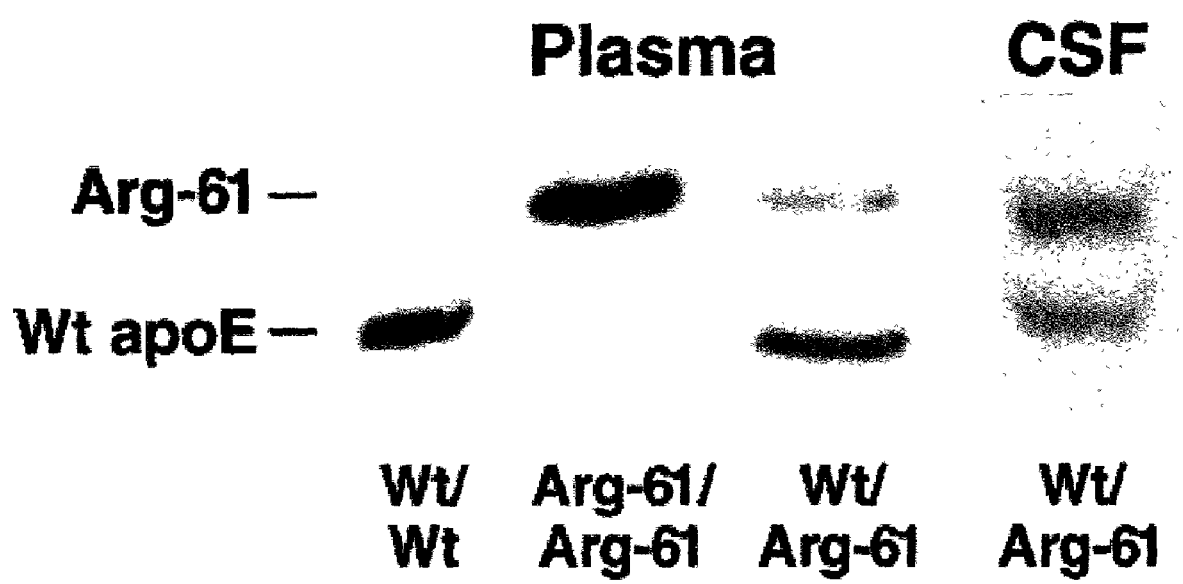
FIG. 2 depicts plasma levels of wild-type mouse apoE and mutant Arg-61 mouse apoE in plasma (left panel) and cerebrospinal fluid (right panel) of wild type (wt/wt), homozygous Arg-61 apoE (Arg-61/Arg-61) and heterozygous Arg-61 (wt/Arg-61) mice.

Isoelectric focusing of wt/wt, wt/Arg-61 and Arg-61/Arg-61 plasma revealed that the Arg-61 apoE focused one charge position in the positive direction as the result of the arginine for threonine substitution, as shown in FIG. 2. This confirms that mutation of the mouse Apoe gene results in expression of the mutant Arg-61 protein. In addition, as shown in FIG. 2, the amount of the Arg-61 apoE in the heterozygous mice was reduced (~70%) compared to wt apoE, reproducing the human heterozygous apoE4/3 phenotype. In contrast, in cerebrospinal fluid (CSF), which does not contain VLDL or any apoB-containing lipoproteins, there were equal levels of the Arg-61 and wt apoE, indicating that the residence times of the two isoforms are very similar in CSF. In further support for the differential metabolism of the Arg-61 and wt mouse apoE in plasma, primary hepatocytes were cultured, and the relative amounts of the two mouse isoforms secreted into the medium were determined by isoelectric focusing. Equal amounts of each isoform were secreted by the hepatocytes.

Since the liver is the primary source of plasma apoE, these results also support the conclusion that the two isoforms are metabolized at different rates in plasma, as a result of domain interaction and the preference of Arg-61 apoE for VLDL and other rapidly cleared lower density lipoproteins.

Figure 3:
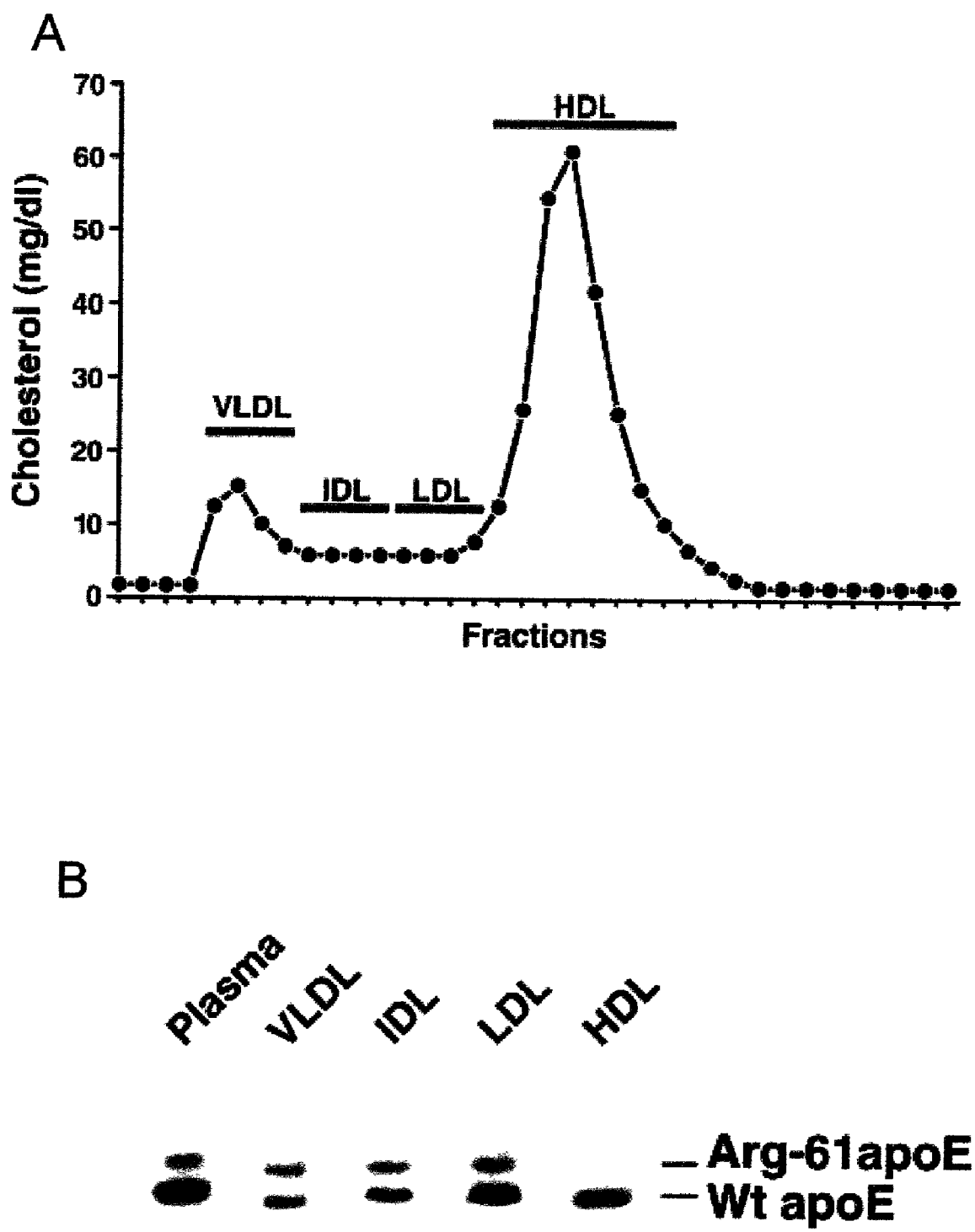
FIG. 3A depicts the FPLC profile of plasma cholesterol distribution.
FIG. 3B depicts distribution of wild-type and Arg-61 apoE in plasma from a heterozygous targeted mouse on a high-cholesterol diet.

To verify the differential binding of Arg-61 apoE for lower density lipoproteins in vivo, we examined the distribution in lipoprotein fractions separated by gel filtration from heterozygous mouse plasma. Since mice are an HDL species, transporting more than 85% of their cholesterol in HDL, they have much lower plasma concentrations of apoB-containing VLDL, intermediate density lipoproteins (IDL), and LDL than humans, where 70–80% of plasma cholesterol is transported in apoB-containing lipoproteins. To increase the plasma concentration of apoB-containing lipoproteins in heterozygous targeted mice, they were fed an atherogenic diet for 6 days. FIG. 3A shows an FPLC profile of plasma cholesterol distribution in these mice. As shown in FIG. 3B, relative to wt apoE the Arg-61 apoE clearly distributed differently, with the majority of the Arg-61 apoE in the lower density apoB-containing lipoproteins. Thus, our results establish that apoE4 domain interaction occurs in vivo in plasma, leading us to the expectation that it will also occur in the CNS.

Figure 4:
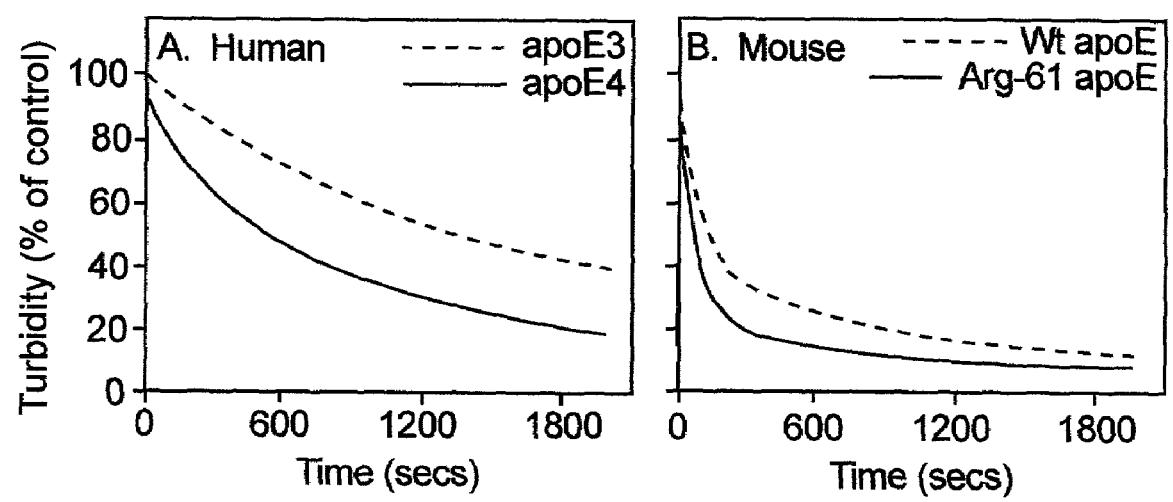
FIGS. 4A and 4B are graphs depicting the ability of human (FIG. 4A), and wild-type and Arg-61 mouse apoE (FIG. 4B) isoforms to bind to dimyristoylphosphatidylcholine (DMPC).

Effect of domain interaction on phospholipid binding activity. Since apoB-containing lipoproteins, including VLDL, do not occur in brain or CSF, it was important to establish that a lipid binding effect resulted from domain interaction in lipoproteins more relevant to the CSF. A common characteristic of soluble plasma apolipoproteins is their ability to clear turbid solutions of phospholipid vesicles to form discoidal lipoprotein complexes. The discoidal complexes formed by apoE resemble the apoE-containing discoidal complexes found in CSF. Pitas et al. (1987) *J. Biol. Chem.* 262:14352–14360; and Rebeck et al. (1998) *Exp. Neurol.* 149:175–182. When we compared the abilities of human apoE3 and apoE4 to clear turbid solutions of phospholipid vesicles of dimyristoylphosphatidylcholine (DMPC), apoE4 was more effective than apoE3, as shown in FIGS. 4A and 4B. Together these results suggest that domain interaction in apoE4 is responsible for its efficacy in binding DMPC. Similarly, when the recombinant Arg-61 mouse apoE was compared with mouse wt apoE, the Arg-61 apoE also bound to DMPC more effectively that wt apoE. These results demonstrate that domain interaction influences the ability of human apoE4 to interact with phospholipid and that the Arg-61 mouse apoE and human apoE4 behave similarly.

In view of the examples presented above, it is clear that the instant invention provides a mouse model for human apoE4 domain interaction, and demonstrates unequivocally that the Arg-61 apoE mouse model displays the expected physiological effects of domain interaction on plasma lipoprotein metabolism, and that mouse Arg-61 apoE mirrors the behavior of human apoE4. Our novel mouse model of human apoE4 provides the opportunity to test the effect of agents that are capable of interfering with the interaction of Arg-61 and Glu-255 in apoE4 thereby converting the closed conformation of apoE4 into an "apoE3-like" open conformation, which agents are useful to treat both cardiovascular diseases and neurodegenerative diseases that are associated with human apoE4.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A gene-targeted mouse whose genome comprises a modified endogenous apolipoprotein E (apoE) allele, wherein said modified allele comprises an apoE-encoding nucleic acid under transcriptional control of endogenous ApoE regulatory sequences, wherein the modified allele encodes a modified apoE polypeptide that exhibits domain interaction characteristic of human apolipoprotein E4 (apoE4), wherein the modified apoE polypeptide comprises a Thr→Arg substitution at a position equivalent to amino acid 61 of human apoE4, wherein the gene targeted mouse is homozygous for the modified apoE allele, and wherein the modified apoE polypeptide exhibits preferential binding to lower density lipoproteins when compared to unmodified, wild-type mouse apoE, and wherein the mouse exhibits apoE4-related neurodegeneration.

2. A cell isolated from the gene-targeted mouse of claim 1, wherein said cell produces the modified apoE polypeptide.

3. A method of identifying an agent that reduces apoE4-related neurodegeneration, the method comprising:
    a) contacting the gene-targeted mouse of claim 1 with a test agent; and
    b) determining the effect of the test agent on reducing apoE4-related neurodegeneration.

4. The cell according to claim 2, wherein said cell is an astrocyte.

5. The cell according to claim 2, wherein said cell is a microglial cell.

6. The cell according to claim 2, wherein the cell is a neuronal cell.

* * * * *

SEQUENCE LISTING

<160> NUMBER OF SEQ ID NOS: 13

<210> SEQ ID NO 1
<211> LENGTH: 299
<212> TYPE: PRT
<213> ORGANISM: homo sapiens

<400> SEQUENCE: 1

Lys Val Glu Gln Ala Val Glu Thr Glu Pro Glu Pro Glu Leu Arg Gln
1               5                   10                  15

Gln Thr Glu Trp Gln Ser Gly Gln Arg Trp Glu Leu Ala Leu Gly Arg
            20                  25                  30

Phe Trp Asp Tyr Leu Arg Trp Val Gln Thr Leu Ser Glu Gln Val Gln
        35                  40                  45

Glu Glu Leu Leu Ser Ser Gln Val Thr Gln Glu Leu Arg Ala Leu Met
    50                  55                  60

Asp Glu Thr Met Lys Glu Leu Lys Ala Tyr Lys Ser Glu Leu Glu Glu
65                  70                  75                  80

Gln Leu Thr Pro Val Ala Glu Glu Thr Arg Ala Arg Leu Ser Lys Glu
                85                  90                  95

Leu Gln Ala Ala Gln Ala Arg Leu Gly Ala Asp Met Glu Asp Val Cys
            100                 105                 110

Gly Arg Leu Val Gln Tyr Arg Gly Glu Val Gln Ala Met Leu Gly Gln
        115                 120                 125

Ser Thr Glu Glu Leu Arg Val Arg Leu Ala Ser His Leu Arg Lys Leu
    130                 135                 140

Arg Lys Arg Leu Leu Arg Asp Ala Asp Asp Leu Gln Lys Arg Leu Ala
145                 150                 155                 160

Val Tyr Gln Ala Gly Ala Arg Glu Gly Ala Glu Arg Gly Leu Ser Ala
                165                 170                 175

Ile Arg Glu Arg Leu Gly Pro Leu Val Glu Gln Gly Arg Val Arg Ala
            180                 185                 190

Ala Thr Val Gly Ser Leu Ala Gly Gln Pro Leu Gln Glu Arg Ala Gln
        195                 200                 205

Ala Trp Gly Glu Arg Leu Arg Ala Arg Met Glu Glu Met Gly Ser Arg
    210                 215                 220

Thr Arg Asp Arg Leu Asp Glu Val Lys Glu Gln Val Ala Glu Val Arg
225                 230                 235                 240

Ala Lys Leu Glu Glu Gln Ala Gln Gln Ile Arg Leu Gln Ala Glu Ala
                245                 250                 255

```
Phe Gln Ala Arg Leu Lys Ser Trp Phe Glu Pro Leu Val Glu Asp Met
            260                 265                 270

Gln Arg Gln Trp Ala Gly Leu Val Glu Lys Val Gln Ala Ala Val Gly
        275                 280                 285

Thr Ser Ala Ala Pro Val Pro Ser Asp Asn His
        290                 295

<210> SEQ ID NO 2
<211> LENGTH: 299
<212> TYPE: PRT
<213> ORGANISM: baboon

<400> SEQUENCE: 2

Lys Val Glu Gln Pro Val Glu Pro Glu Thr Glu Pro Asp Val Arg Gln
  1               5                  10                  15

Gln Ala Glu Trp Gln Ser Gly Gln Pro Trp Glu Leu Ala Leu Gly Arg
             20                  25                  30

Phe Trp Asp Tyr Leu Arg Trp Val Gln Thr Leu Ser Glu Gln Val Gln
         35                  40                  45

Glu Glu Leu Leu Ser Pro Gln Val Thr Gln Glu Leu Thr Thr Leu Met
 50                  55                  60

Asp Glu Thr Met Lys Glu Leu Lys Ala Tyr Lys Ser Glu Leu Glu Glu
 65                  70                  75                  80

Gln Leu Ser Pro Val Ala Glu Glu Thr Arg Ala Arg Leu Ser Lys Glu
                 85                  90                  95

Leu Gln Ala Ala Gln Ala Arg Leu Gly Ala Asp Met Glu Asp Val Arg
            100                 105                 110

Ser Arg Leu Val Gln Tyr Arg Ser Glu Val Gln Ala Met Leu Gly Gln
        115                 120                 125

Ser Thr Glu Glu Leu Arg Ala Arg Leu Ala Ser His Leu Arg Lys Leu
130                 135                 140

Arg Lys Arg Leu Leu Arg Asp Ala Asp Asp Leu Gln Lys Arg Leu Ala
145                 150                 155                 160

Val Tyr Gln Ala Gly Ala Arg Glu Gly Ala Glu Arg Gly Val Ser Ala
                165                 170                 175

Ile Arg Glu Arg Leu Gly Pro Leu Val Glu Gln Gly Arg Val Arg Ala
            180                 185                 190

Ala Thr Val Gly Ser Leu Ala Ser Gln Pro Leu Gln Glu Arg Ala Gln
        195                 200                 205

Ala Leu Gly Glu Arg Leu Arg Ala Arg Met Glu Glu Met Gly Ser Arg
    210                 215                 220

Thr Arg Asp Arg Leu Asp Glu Val Lys Glu Gln Val Ala Glu Val Arg
225                 230                 235                 240

Ala Lys Leu Glu Glu Gln Ala Gln Gln Ile Ser Leu Gln Ala Glu Ala
                245                 250                 255

Phe Gln Ala Arg Leu Lys Ser Trp Phe Glu Pro Leu Val Glu Asp Met
            260                 265                 270

Gln Arg Gln Trp Ala Gly Leu Val Glu Lys Val Gln Ala Ala Val Gly
        275                 280                 285

Ala Ser Thr Ala Pro Val Pro Ser Asp Asn His
    290                 295

<210> SEQ ID NO 3
<211> LENGTH: 299
<212> TYPE: PRT
<213> ORGANISM: CYNOMOLGUS MONKEY
```

<400> SEQUENCE: 3

Lys Val Glu Gln Pro Val Pro Glu Thr Glu Pro Glu Leu Arg Gln
1               5                   10                  15

Gln Ala Glu Gly Gln Ser Gly Gln Pro Trp Glu Leu Ala Leu Gly Arg
            20                  25                  30

Phe Trp Asp Tyr Leu Arg Trp Val Gln Thr Leu Ser Glu Gln Val Gln
            35                  40                  45

Glu Glu Leu Leu Ser Pro Gln Val Thr Gln Glu Leu Thr Thr Leu Met
50                  55                  60

Asp Glu Thr Met Lys Glu Leu Lys Ala Tyr Lys Ser Glu Leu Glu Glu
65                  70                  75                  80

Gln Leu Ser Pro Val Ala Glu Glu Thr Arg Ala Arg Leu Ser Lys Glu
                85                  90                  95

Leu Gln Ala Ala Gln Ala Arg Leu Gly Ala Asp Met Glu Asp Val Arg
            100                 105                 110

Ser Arg Leu Val Gln Tyr Arg Ser Glu Val Gln Ala Met Leu Gly Gln
            115                 120                 125

Ser Thr Glu Glu Leu Arg Ala Arg Leu Ala Ser His Leu Arg Lys Leu
130                 135                 140

Arg Lys Arg Leu Leu Arg Asp Ala Asp Asp Leu Gln Lys Arg Leu Ala
145                 150                 155                 160

Val Tyr Gln Ala Gly Ala Arg Glu Gly Ala Glu Arg Gly Val Ser Ala
                165                 170                 175

Ile Arg Glu Arg Leu Gly Pro Leu Val Glu Gln Gly Arg Val Arg Ala
            180                 185                 190

Ala Thr Val Gly Ser Leu Ala Ser Gln Pro Leu Gln Glu Arg Ala Gln
            195                 200                 205

Ala Leu Gly Glu Arg Leu Arg Ala Arg Met Glu Glu Met Gly Ser Arg
210                 215                 220

Thr Arg Asp Arg Leu Asp Glu Val Lys Glu Gln Val Ala Glu Val Arg
225                 230                 235                 240

Ala Lys Leu Glu Glu Gln Ala Gln Gln Ile Ser Leu Gln Ala Glu Ala
                245                 250                 255

Phe Gln Ala Arg Leu Lys Ser Trp Phe Glu Pro Leu Val Glu Asp Met
            260                 265                 270

Gln Arg Gln Trp Ala Gly Leu Val Glu Lys Val Gln Ala Ala Val Gly
            275                 280                 285

Ala Ser Thr Ala Pro Val Pro Ile Asp Asn His
290                 295

<210> SEQ ID NO 4
<211> LENGTH: 293
<212> TYPE: PRT
<213> ORGANISM: rat

<400> SEQUENCE: 4

Glu Gly Glu Leu Glu Val Thr Asp Gln Leu Pro Gly Gln Ser Asp Gln
1               5                   10                  15

Pro Trp Glu Gln Ala Leu Asn Arg Phe Trp Asp Tyr Leu Arg Trp Val
            20                  25                  30

Gln Thr Leu Ser Asp Gln Val Gln Glu Glu Leu Gln Ser Ser Gln Val
            35                  40                  45

Thr Gln Glu Leu Thr Val Leu Met Glu Asp Thr Met Thr Glu Val Lys
50                  55                  60

```
Ala Tyr Lys Lys Glu Leu Glu Glu Gln Leu Gly Pro Val Ala Glu Glu
 65                  70                  75                  80

Thr Arg Ala Arg Leu Thr Lys Glu Val Gln Ala Ala Gln Ala Arg Leu
                 85                  90                  95

Gly Ala Asp Met Glu Asp Leu Arg Asn Arg Leu Gly Gln Tyr Arg Asn
            100                 105                 110

Glu Val Asn Thr Met Leu Gly Gln Ser Thr Glu Glu Leu Arg Ser Arg
        115                 120                 125

Leu Ser Thr His Leu Arg Lys Met Arg Lys Arg Leu Met Arg Asp Ala
130                 135                 140

Asp Asp Leu Gln Lys Arg Leu Ala Val Tyr Lys Ala Gly Ala Gln Glu
145                 150                 155                 160

Gly Ala Glu Arg Gly Val Ser Ala Ile Arg Glu Arg Leu Gly Pro Leu
                165                 170                 175

Val Glu Gln Gly Arg Gln Arg Thr Ala Asn Leu Arg Trp Arg Arg Pro
            180                 185                 190

Ala Pro Arg Asp Arg Ala Gln Ala Leu Ser Asp Arg Ile Arg Gly Arg
        195                 200                 205

Leu Glu Glu Val Gly Asn Gln Ala Arg Asp Arg Leu Glu Glu Val Arg
210                 215                 220

Glu Gln Met Glu Glu Val Arg Ser Lys Met Glu Glu Gln Thr Gln Gln
225                 230                 235                 240

Ile Arg Leu Gln Ala Glu Ile Phe Gln Ala Arg Ile Lys Gly Trp Phe
                245                 250                 255

Glu Pro Leu Val Glu Asp Met Gln Arg Gln Trp Ala Asn Leu Met Glu
            260                 265                 270

Lys Ile Gln Ala Ser Val Ala Thr Asn Ser Ile Ala Ser Thr Thr Val
        275                 280                 285

Pro Leu Glu Asn Gln
    290

<210> SEQ ID NO 5
<211> LENGTH: 293
<212> TYPE: PRT
<213> ORGANISM: mouse

<400> SEQUENCE: 5

Glu Gly Glu Pro Glu Val Thr Asp Gln Leu Glu Trp Gln Ser Asn Gln
 1               5                  10                  15

Pro Trp Glu Gln Ala Leu Asn Arg Phe Trp Asp Tyr Leu Arg Trp Val
                20                  25                  30

Gln Thr Leu Ser Asp Gln Val Gln Glu Glu Leu Gln Ser Ser Gln Val
            35                  40                  45

Thr Gln Glu Leu Thr Ala Leu Met Glu Asp Thr Met Thr Glu Val Lys
        50                  55                  60

Ala Tyr Lys Lys Glu Leu Glu Glu Gln Leu Gly Pro Val Ala Glu Glu
 65                  70                  75                  80

Thr Arg Ala Arg Leu Gly Lys Glu Val Gln Ala Ala Gln Ala Arg Leu
                 85                  90                  95

Gly Ala Asp Met Glu Asp Leu Arg Asn Arg Leu Gly Gln Tyr Arg Asn
            100                 105                 110

Glu Val His Thr Met Leu Gly Gln Ser Thr Glu Glu Ile Arg Ala Arg
        115                 120                 125

Leu Ser Thr His Leu Arg Lys Met Arg Lys Arg Leu Met Arg Asp Ala
```

```
                130                 135                 140
Asp Asp Leu Gln Lys Arg Leu Ala Val Tyr Lys Ala Gly Ala Arg Glu
145                 150                 155                 160

Gly Ala Glu Arg Gly Val Ser Ala Ile Arg Glu Arg Leu Gly Pro Leu
                165                 170                 175

Val Glu Gln Gly Arg Gln Arg Thr Ala Asn Leu Gly Ala Gly Ala Ala
                180                 185                 190

Gln Pro Leu Arg Asp Arg Ala Gln Ala Phe Gly Asp Arg Ile Arg Gly
                195                 200                 205

Arg Leu Glu Glu Val Gly Asn Gln Ala Arg Asp Arg Leu Glu Glu Val
210                 215                 220

Arg Glu His Met Glu Glu Val Arg Ser Lys Met Glu Glu Gln Thr Gln
225                 230                 235                 240

Gln Ile Arg Leu Gln Ala Glu Ile Phe Gln Ala Arg Leu Lys Gly Trp
                245                 250                 255

Phe Glu Pro Ile Val Glu Asp Met His Arg Gln Trp Ala Asn Leu Met
                260                 265                 270

Glu Lys Ile Gln Ala Ser Val Ala Thr Asn Pro Ile Ile Thr Pro Val
                275                 280                 285

Ala Gln Glu Asn Gln
            290

<210> SEQ ID NO 6
<211> LENGTH: 280
<212> TYPE: PRT
<213> ORGANISM: GUINEA PIG

<400> SEQUENCE: 6

Asp Val Glu Pro Glu Val Glu Val Arg Glu Pro Ala Val Trp Gln Ser
1               5                   10                  15

Gly Gln Pro Trp Glu Leu Ala Leu Ser Arg Phe Trp Asp Tyr Leu Arg
                20                  25                  30

Trp Val Gln Thr Leu Ser Asp Gln Val Gln Glu Glu Leu Leu Ser Asn
            35                  40                  45

Gln Val Thr Gln Glu Leu Thr Leu Leu Ile Glu Asp Thr Met Lys Glu
        50                  55                  60

Val Lys Ala Tyr Lys Ala Glu Leu Glu Lys Glu Leu Gly Pro Val Ala
65                  70                  75                  80

Glu Asp Thr Lys Ala Arg Leu Ala Lys Glu Leu Gln Ala Ala Gln Ala
                85                  90                  95

Arg Leu Gly Ala Asp Met Glu Glu Val Arg Asn Arg Leu Ser Gln Tyr
                100                 105                 110

Arg Ser Glu Val Gln Ala Met Leu Gly Gln Ser Ser Glu Glu Leu Arg
            115                 120                 125

Ala Arg Leu Thr Ser His Pro Arg Lys Met Lys Arg Leu Gln Arg
        130                 135                 140

Asp Ile Asp Glu Leu Gln Lys Arg Met Ala Val Tyr Lys Ala Gly Ala
145                 150                 155                 160

Gln Glu Gly Ala Glu Arg Gly Val Ser Ala Ile Arg Glu Arg Leu Gly
                165                 170                 175

Ser Leu Ile Glu Gln Gly Arg Leu Gln Ala Leu Ala Ser Gln Pro Leu
                180                 185                 190

Gln Glu Arg Ala Gln Ala Trp Gly Glu Gln Met Arg Gly Arg Leu Glu
            195                 200                 205
```

```
Lys Val Gly Ser Gln Ala Arg Asp Arg Leu Glu Glu Val Arg Glu Gln
    210                 215                 220

Met Glu Glu Val Arg Val Lys Val Glu Glu Gln Ala Glu Ala Phe Gln
225                 230                 235                 240

Ala Arg Leu Lys Ser Trp Phe Glu Pro Met Met Glu Asp Met Arg Arg
                245                 250                 255

Gln Trp Ala Glu Leu Ile Gln Lys Val Gln Val Ala Val Gly Ala Ser
                260                 265                 270

Thr Ser Ala Pro Ser Gln Glu Pro
        275                 280

<210> SEQ ID NO 7
<211> LENGTH: 293
<212> TYPE: PRT
<213> ORGANISM: rabbit

<400> SEQUENCE: 7

Glu Thr Glu Gln Glu Val Glu Val Pro Glu Gln Ala Arg Trp Lys Ala
  1               5                  10                  15

Gly Gln Pro Trp Glu Leu Ala Leu Gly Arg Phe Trp Asp Tyr Leu Arg
                20                  25                  30

Trp Val Gln Ser Leu Ser Asp Gln Val Gln Glu Glu Leu Leu Ser Ser
                35                  40                  45

Gln Val Thr Gln Glu Leu Thr Met Leu Met Glu Glu Thr Met Lys Glu
    50                  55                  60

Val Lys Ala Tyr Lys Ser Glu Leu Glu Glu Gln Leu Ser Pro Met Ala
65                  70                  75                  80

Gln Glu His Arg Ala Arg Leu Ser Lys Glu Leu Gln Val Ala Gly Ala
                85                  90                  95

Leu Glu Ala Asp Met Glu Asp Val Cys Asn Arg Leu Ala Gln Tyr Arg
                100                 105                 110

Gly Glu Ala Gln Ala Met Leu Gly Gln Ser Thr Glu Glu Leu Ala Arg
                115                 120                 125

Ala Phe Ser Ser His Leu Arg Lys Leu Arg Lys Arg Leu Leu Arg Asp
    130                 135                 140

Ala Glu Asp Leu Gln Lys Arg Met Ala Val Tyr Gly Ala Gly Ala Arg
145                 150                 155                 160

Glu Gly Ala Glu Arg Gly Val Ser Ala Val Arg Glu Arg Leu Gly Ser
                165                 170                 175

Arg Leu Glu Arg Gly Arg Leu Arg Val Ala Thr Val Gly Thr Leu Ala
                180                 185                 190

Gly Arg Pro Leu Arg Glu Arg Ala Gln Ala Trp Gly Glu Arg Leu Arg
                195                 200                 205

Gly His Leu Glu Glu Val Gly Ser Arg Ala Arg Asp Arg Leu Asn Glu
    210                 215                 220

Val Arg Glu Gln Val Glu Glu Val Arg Val Lys Val Glu Glu Gln Ala
225                 230                 235                 240

Pro Gln Met Arg Leu Gln Ala Glu Ala Phe Gln Ala Arg Leu Lys Ser
                245                 250                 255

Trp Phe Glu Pro Leu Val Glu Asp Met Gln Arg Gln Trp Ala Gly Leu
                260                 265                 270

Val Glu Lys Leu Gln Ala Ala Met Pro Ser Lys Ala Pro Ala Ala Ala
    275                 280                 285

Pro Ile Glu Asn Gln
    290
```

<210> SEQ ID NO 8
<211> LENGTH: 298
<212> TYPE: PRT
<213> ORGANISM: cow

<400> SEQUENCE: 8

```
Asp Met Glu Gly Glu Leu Gly Pro Glu Pro Leu Thr Thr Gln Gln
 1               5                  10                  15

Pro Arg Gly Lys Asp Ser Gln Pro Trp Glu Gln Ala Leu Gly Arg Phe
            20                  25                  30

Trp Asp Tyr Leu Arg Trp Val Gln Thr Leu Ser Asp Gln Val Gln Glu
        35                  40                  45

Glu Leu Leu Asn Thr Gln Val Ile Gln Glu Leu Thr Ala Leu Met Glu
    50                  55                  60

Glu Thr Met Lys Glu Val Lys Ala Tyr Lys Glu Glu Leu Glu Gly Gln
65                  70                  75                  80

Leu Gly Pro Met Ala Gln Glu Thr Gln Ala Arg Val Ser Lys Glu Leu
                85                  90                  95

Gln Ala Ala Gln Ala Arg Leu Gly Ser Asp Met Glu Asp Leu Arg Asn
            100                 105                 110

Arg Leu Ala Gln Tyr Arg Ser Glu Val Gln Ala Met Leu Gly Gln Ser
        115                 120                 125

Thr Glu Glu Leu Arg Ala Arg Met Ala Ser His Leu Arg Lys Leu Pro
    130                 135                 140

Lys Arg Leu Leu Arg Asp Ala Asp Asp Leu Lys Lys Arg Leu Ala Val
145                 150                 155                 160

Tyr Gln Ala Gly Ala Ser Glu Gly Ala Glu Arg Ser Leu Ser Ala Ile
                165                 170                 175

Arg Glu Arg Phe Gly Pro Leu Val Glu Gln Gly Gln Ser Arg Ala Ala
            180                 185                 190

Thr Leu Ser Thr Leu Ala Gly Gln Pro Leu Leu Glu Arg Ala Glu Ala
        195                 200                 205

Trp Arg Gln Lys Leu His Gly Arg Leu Glu Glu Val Gly Val Arg Ala
    210                 215                 220

Gln Asp Arg Leu Asp Lys Ile Arg Gln Gln Leu Glu Glu Val His Ala
225                 230                 235                 240

Lys Val Glu Glu Gln Gly Asn Gln Met Arg Leu Gln Ala Glu Ala Phe
                245                 250                 255

Gln Ala Arg Leu Arg Ser Trp Phe Glu Pro Leu Val Glu Asp Met Gln
            260                 265                 270

Arg Gln Trp Ala Gly Leu Val Glu Lys Val Gln Leu Ala Leu Arg Pro
        275                 280                 285

Ser Pro Thr Ser Pro Ser Glu Asn His
    290                 295
```

<210> SEQ ID NO 9
<211> LENGTH: 291
<212> TYPE: PRT
<213> ORGANISM: dog

<400> SEQUENCE: 9

```
Lys Val Gln Gln Glu Leu Glu Pro Glu Ala Gly Trp Gln Thr Gly Gln
 1               5                  10                  15

Pro Trp Glu Ala Ala Leu Ala Arg Phe Trp Asp Tyr Leu Arg Trp Val
            20                  25                  30
```

```
Gln Thr Leu Ser Asp Gln Val Gln Glu Gly Val Leu Asn Thr Gln Val
        35                  40                  45

Thr Gln Glu Leu Thr Ala Leu Met Asp Glu Thr Met Lys Glu Val Lys
 50                  55                  60

Ala Tyr Lys Ala Glu Leu Asp Glu Gln Leu Gly Pro Met Thr Ser Glu
65                  70                  75                  80

Thr Gln Ala Arg Val Ala Lys Glu Leu Gln Ala Gln Ala Arg Leu
                85                  90                  95

Arg Ala Asp Met Glu Asp Val Arg Asn Arg Leu Thr Gln Tyr Arg Gly
                100                 105                 110

Glu Leu Gln Ala Met Leu Gly Gln Ser Ser Glu Glu Leu Arg Ala Arg
            115                 120                 125

Phe Ala Ser His Met Arg Lys Leu Arg Lys Arg Val Leu Arg Asp Ala
        130                 135                 140

Glu Asp Leu Gln Arg Arg Leu Ala Val Tyr Lys Ala Gly Val Arg Glu
145                 150                 155                 160

Gly Ala Glu Arg Ser Val Ser Ser Ile Arg Glu Arg Leu Trp Pro Leu
                165                 170                 175

Leu Glu Gln Ala Arg Glu Arg Asn Ala Lys Val Gly Ala Leu Ala Thr
            180                 185                 190

Gln Pro Leu Leu Glu Arg Ala Asp Ala Trp Gly Gln Gln Leu Arg Gly
        195                 200                 205

Gln Leu Glu Glu Met Ser Ser Arg Ala Arg Gly His Leu Glu Glu Met
    210                 215                 220

Arg Glu Gln Ile Gln Glu Val Arg Val Lys Met Glu Glu Gln Ala Asp
225                 230                 235                 240

Gln Ile Arg Gln Lys Ala Glu Ala Phe Gln Ala Arg Leu Lys Ser Trp
                245                 250                 255

Phe Glu Pro Leu Leu Glu Asp Met Gln Arg Gln Trp Asp Gly Leu Val
            260                 265                 270

Glu Lys Val Gln Ala Ala Val Ala Thr Ile Pro Thr Ser Lys Pro Val
        275                 280                 285

Glu Glu Pro
    290

<210> SEQ ID NO 10
<211> LENGTH: 291
<212> TYPE: PRT
<213> ORGANISM: sea lion

<400> SEQUENCE: 10

Glu Leu Glu Gln Glu Val Glu Pro Glu Ala Gly Trp Gln Ala Gly Gln
 1               5                   10                  15

Pro Trp Glu Leu Ala Leu Ala Arg Phe Trp Asp Tyr Leu Arg Trp Val
            20                  25                  30

Gln Thr Leu Ser Asp Gln Val Gln Glu Val Leu Ser Asn Gln Val
        35                  40                  45

Thr Gln Glu Leu Thr Thr Leu Met Glu Glu Thr Met Lys Glu Ile Lys
 50                  55                  60

Ala Tyr Arg Ala Glu Leu Glu Glu Gln Leu Gly Pro Met Ala Ser Glu
65                  70                  75                  80

Thr Gln Ala Arg Val Ala Lys Glu Leu Gln Ala Gln Ala Arg Leu
                85                  90                  95
```

-continued

```
Arg Ser Asp Met Glu Asp Val Arg Thr Arg Leu Ser Gln Tyr Arg Gly
            100                 105                 110
Glu Val Gln Ala Met Leu Gly Gln Ser Thr Glu Glu Leu Arg Ala Arg
        115                 120                 125
Phe Ala Ser His Met Arg Lys Leu Arg Lys Arg Val Leu Arg Asp Ala
    130                 135                 140
Glu Asp Leu Gln Lys Arg Leu Ala Val Tyr Arg Ala Gly Val Arg Glu
145                 150                 155                 160
Gly Ala Glu Arg Ser Val Ser Thr Ile Arg Glu Arg Leu Trp Pro Leu
                165                 170                 175
Leu Glu Gln Ala Arg Thr Arg His Ala Lys Val Asp Ala Leu Ala Thr
            180                 185                 190
Gln Pro Leu Arg Glu Arg Val Asn Ala Leu Gly Gln Gln Leu Arg Gly
        195                 200                 205
Arg Leu Glu Glu Val Gly Ser Arg Ala Arg Ser His Leu Asp Glu Val
    210                 215                 220
Arg Glu Gln Met Glu Glu Val Gln Ala Lys Met Glu Glu Gln Ala Asn
225                 230                 235                 240
Gln Met Arg Gln Gln Ala Glu Ala Phe Gln Ala Arg Leu Lys Gly Trp
                245                 250                 255
Phe Glu Pro Leu Val Glu Asp Met Gln Arg Gln Trp Ala Val Leu Val
            260                 265                 270
Glu Lys Val Gln Ala Ala Val Gly Thr Ser Pro Thr Thr Pro Pro Val
        275                 280                 285
Glu Thr Lys
    290

<210> SEQ ID NO 11
<211> LENGTH: 14
<212> TYPE: PRT
<213> ORGANISM: dog

<400> SEQUENCE: 11

Asp Val Gln Pro Glu Pro Glu Leu Glu Arg Glu Leu Glu Pro
1               5                   10

<210> SEQ ID NO 12
<211> LENGTH: 16
<212> TYPE: PRT
<213> ORGANISM: sea lion

<400> SEQUENCE: 12

Asp Val Glu Pro Glu Ser Pro Leu Glu Glu Asn Leu Glu Pro Glu Leu
1               5                   10                  15

<210> SEQ ID NO 13
<211> LENGTH: 4
<212> TYPE: PRT
<213> ORGANISM: sea lion

<400> SEQUENCE: 13

Glu Pro Lys Arg
1
```